(12) United States Patent
Budiman et al.

(10) Patent No.: US 12,279,866 B2
(45) Date of Patent: *Apr. 22, 2025

(54) SENSITIVITY CALIBRATION OF IN VIVO SENSORS USED TO MEASURE ANALYTE CONCENTRATION

(71) Applicant: ABBOTT DIABETES CARE INC., Alameda, CA (US)

(72) Inventors: Erwin Satrya Budiman, Fremont, CA (US); Gary Alan Hayter, Oakland, CA (US)

(73) Assignee: ABBOTT DIABETES CARE INC., Alameda, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/580,579

(22) Filed: Jan. 20, 2022

(65) Prior Publication Data

US 2022/0142518 A1 May 12, 2022

Related U.S. Application Data

(63) Continuation of application No. 16/256,855, filed on Jan. 24, 2019, which is a continuation of application
(Continued)

(51) Int. Cl.
*A61B 5/1495* (2006.01)
*A61B 5/00* (2006.01)
(Continued)

(52) U.S. Cl.
CPC ........ *A61B 5/1495* (2013.01); *A61B 5/14532* (2013.01); *A61B 5/14546* (2013.01);
(Continued)

(58) Field of Classification Search
CPC .............. A61B 5/1495; A61B 5/14532; A61B 2560/0228; G16H 40/40
See application file for complete search history.

(56) References Cited

U.S. PATENT DOCUMENTS 683,553 A 10/1901 Carter
3,581,062 A 5/1971 Aston
(Continued)

FOREIGN PATENT DOCUMENTS

EP 0098592 1/1984
EP 0127958 12/1984
(Continued)

OTHER PUBLICATIONS

U.S. Appl. No. 61/227,967, filed Jul. 23, 2009, Hoss, et al.
(Continued)

*Primary Examiner* — Christian Jang
(74) *Attorney, Agent, or Firm* — Baker Botts L.L.P.

(57) ABSTRACT

Methods, devices, systems, and computer program products are provided to improve sensitivity calibration of an in vivo analyte sensor and usability of an associated analyte monitoring system. In certain embodiments, methods are provided that improve the user experience of using an analyte monitoring system. Certain embodiments of the present disclosure include features that reduce the amount of calibration or re-calibration performed by the analyte monitoring system. More specifically methods of using a suspect calibration attempt to avoid having to recalibrate by adjusting the calibration or mitigating effects of sensor signal attenuation that caused the calibration attempt to be suspect are provided. Additional features are disclosed.

32 Claims, 12 Drawing Sheets

Related U.S. Application Data

No. 15/789,949, filed on Oct. 20, 2017, now Pat. No. 10,188,334, which is a continuation of application No. 15/616,916, filed on Jun. 7, 2017, now Pat. No. 9,801,577, which is a continuation of application No. 14/066,650, filed on Oct. 29, 2013, now Pat. No. 9,675,290.

(60) Provisional application No. 61/720,393, filed on Oct. 30, 2012.

(51) Int. Cl.
  *A61B 5/145*   (2006.01)
  *G16H 40/40*   (2018.01)

(52) U.S. Cl.
  CPC .............. *A61B 5/742* (2013.01); *G16H 40/40* (2018.01); *A61B 2560/0223* (2013.01); *A61B 2560/0228* (2013.01)

(56) References Cited

U.S. PATENT DOCUMENTS

| | | |
|---|---|---|
| 3,926,760 A | 12/1975 | Allen et al. |
| 3,949,388 A | 4/1976 | Fuller |
| 3,960,497 A | 6/1976 | Acord et al. |
| 3,978,856 A | 9/1976 | Michel |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,441,968 A | 4/1984 | Emmer et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,650,547 A | 3/1987 | Gough |
| 4,671,288 A | 6/1987 | Gough |
| 4,703,756 A | 11/1987 | Gough et al. |
| 4,711,245 A | 12/1987 | Higgins et al. |
| 4,731,051 A | 3/1988 | Fischell |
| 4,731,726 A | 3/1988 | Allen, III |
| 4,749,985 A | 6/1988 | Corsberg |
| 4,750,496 A | 6/1988 | Reinhart et al. |
| 4,757,022 A | 7/1988 | Shults et al. |
| 4,759,366 A | 7/1988 | Callaghan |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,947,845 A | 8/1990 | Davis |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,034,112 A | 7/1991 | Murase et al. |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,089,112 A | 2/1992 | Skotheim et al. |
| 5,106,365 A | 4/1992 | Hernandez |
| 5,113,869 A | 5/1992 | Nappholz et al. |
| 5,122,925 A | 6/1992 | Inpyn |
| 5,135,004 A | 8/1992 | Adams et al. |
| 5,145,381 A | 9/1992 | Volz |
| 5,148,812 A | 9/1992 | Verrier et al. |
| 5,165,407 A | 11/1992 | Wilson et al. |
| 5,199,428 A | 4/1993 | Obel et al. |
| 5,202,261 A | 4/1993 | Musho et al. |
| 5,203,326 A | 4/1993 | Collins |
| 5,204,264 A | 4/1993 | Kaminer et al. |
| 5,210,778 A | 5/1993 | Massart |
| 5,231,988 A | 8/1993 | Wernicke et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,313,953 A | 5/1994 | Yomtov et al. |
| 5,320,715 A | 6/1994 | Berg |
| 5,320,725 A | 6/1994 | Gregg et al. |
| 5,322,063 A | 6/1994 | Allen et al. |
| 5,328,460 A | 7/1994 | Lord et al. |
| 5,330,634 A | 7/1994 | Wong et al. |
| 5,340,722 A | 8/1994 | Wolfbeis et al. |
| 5,342,789 A | 8/1994 | Chick et al. |
| 5,352,351 A | 10/1994 | White et al. |
| 5,354,449 A | 10/1994 | Band et al. |
| 5,356,786 A | 10/1994 | Heller et al. |
| 5,360,404 A | 11/1994 | Novacek et al. |
| 5,365,426 A | 11/1994 | Siegel et al. |
| 5,372,427 A | 12/1994 | Padovani et al. |
| 5,376,070 A | 12/1994 | Purvis et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,400,795 A | 3/1995 | Murphy et al. |
| 5,408,999 A | 4/1995 | Singh et al. |
| 5,411,647 A | 5/1995 | Johnson et al. |
| 5,425,749 A | 6/1995 | Adams |
| 5,425,868 A | 6/1995 | Pedersen |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,520,191 A | 5/1996 | Karlsson et al. |
| 5,531,878 A | 7/1996 | Vadgama et al. |
| 5,532,686 A | 7/1996 | Urbas et al. |
| 5,543,326 A | 8/1996 | Heller et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,890 A | 5/1997 | Carter et al. |
| 5,634,468 A | 6/1997 | Platt et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |

(56) References Cited

U.S. PATENT DOCUMENTS

| | | |
|---|---|---|
| 5,695,623 A | 12/1997 | Michel et al. |
| 5,707,502 A | 1/1998 | McCaffrey et al. |
| 5,711,001 A | 1/1998 | Bussan et al. |
| 5,711,861 A | 1/1998 | Ward et al. |
| 5,720,295 A | 2/1998 | Greenhut et al. |
| 5,724,030 A | 3/1998 | Urbas et al. |
| 5,733,259 A | 3/1998 | Valcke et al. |
| 5,735,285 A | 4/1998 | Albert et al. |
| 5,741,211 A | 4/1998 | Renirie et al. |
| 5,749,907 A | 5/1998 | Mann |
| 5,772,586 A | 6/1998 | Heinonen et al. |
| 5,785,660 A | 7/1998 | van Lake et al. |
| 5,786,439 A | 7/1998 | Van Antwerp et al. |
| 5,791,344 A | 8/1998 | Schulman et al. |
| 5,792,065 A | 8/1998 | Xue et al. |
| 5,804,047 A | 9/1998 | Karube et al. |
| 5,820,551 A | 10/1998 | Hill et al. |
| 5,822,715 A | 10/1998 | Worthington et al. |
| 5,863,400 A | 1/1999 | Drummond et al. |
| 5,891,047 A | 4/1999 | Lander et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,960,797 A | 10/1999 | Kramer et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,016,443 A | 1/2000 | Ekwall et al. |
| 6,021,350 A | 2/2000 | Mathson |
| 6,024,699 A | 2/2000 | Surwit et al. |
| 6,038,469 A | 3/2000 | Karlsson et al. |
| 6,049,727 A | 4/2000 | Crothall |
| 6,071,391 A | 6/2000 | Gotoh et al. |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,103,033 A | 8/2000 | Say et al. |
| 6,108,577 A | 8/2000 | Benser |
| 6,112,116 A | 8/2000 | Fischell |
| 6,115,622 A | 9/2000 | Minoz |
| 6,115,628 A | 9/2000 | Stadler et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,128,526 A | 10/2000 | Stadler et al. |
| 6,130,623 A | 10/2000 | MacLellan et al. |
| 6,134,461 A | 10/2000 | Say et al. |
| 6,143,164 A | 11/2000 | Heller et al. |
| 6,144,837 A | 11/2000 | Quy |
| 6,144,871 A | 11/2000 | Saito et al. |
| 6,159,147 A | 12/2000 | Lichter et al. |
| 6,161,095 A | 12/2000 | Brown |
| 6,162,611 A | 12/2000 | Heller et al. |
| 6,168,957 B1 | 1/2001 | Matzinger et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,212,417 B1 | 4/2001 | Ikeda et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,233,486 B1 | 5/2001 | Ekwall et al. |
| 6,237,394 B1 | 5/2001 | Harris et al. |
| 6,248,067 B1 | 6/2001 | Causey, III et al. |
| 6,249,705 B1 | 6/2001 | Snell |
| 6,254,586 B1 | 7/2001 | Mann et al. |
| 6,256,538 B1 | 7/2001 | Ekwall |
| 6,264,606 B1 | 7/2001 | Ekwall et al. |
| 6,270,455 B1 | 8/2001 | Brown |
| 6,272,379 B1 | 8/2001 | Fischell et al. |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,361,503 B1 | 3/2002 | Starobin et al. |
| 6,366,794 B1 | 4/2002 | Moussy et al. |
| 6,368,141 B1 | 4/2002 | VanAntwerp et al. |
| 6,377,828 B1 | 4/2002 | Chaiken et al. |
| 6,377,852 B1 | 4/2002 | Bornzin et al. |
| 6,377,894 B1 | 4/2002 | Deweese et al. |
| 6,379,301 B1 | 4/2002 | Worthington et al. |
| 6,381,493 B1 | 4/2002 | Stadler et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,475,372 B1 | 11/2002 | Ohara et al. |
| 6,475,750 B1 | 11/2002 | Han et al. |
| 6,478,736 B1 | 11/2002 | Mault |
| 6,484,046 B1 | 11/2002 | Say et al. |
| 6,496,729 B2 | 12/2002 | Thompson |
| 6,497,655 B1 | 12/2002 | Linberg et al. |
| 6,501,983 B1 | 12/2002 | Natarajan et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,522,903 B1 | 2/2003 | Berman et al. |
| 6,540,891 B1 | 4/2003 | Stewart et al. |
| 6,544,212 B2 | 4/2003 | Galley et al. |
| 6,549,796 B2 | 4/2003 | Sohrab |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,587,704 B1 | 7/2003 | Fine et al. |

(56) References Cited

U.S. PATENT DOCUMENTS

| | | |
|---|---|---|
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,622,045 B2 | 9/2003 | Snell et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,721,582 B2 | 4/2004 | Trepagnier et al. |
| 6,730,200 B1 | 5/2004 | Stewart et al. |
| 6,731,976 B2 | 5/2004 | Penn et al. |
| 6,731,985 B2 | 5/2004 | Poore et al. |
| 6,733,446 B2 | 5/2004 | Lebel et al. |
| 6,735,183 B2 | 5/2004 | O'Toole et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,850,859 B1 | 2/2005 | Schuh |
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,912,413 B2 | 6/2005 | Rantala et al. |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman, IV et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,010,345 B2 | 3/2006 | Hill et al. |
| 7,011,630 B2 | 3/2006 | Desai et al. |
| 7,016,713 B2 | 3/2006 | Gardner et al. |
| 7,016,720 B2 | 3/2006 | Kroll |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,029,443 B2 | 4/2006 | Kroll |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,043,305 B2 | 5/2006 | KenKnight et al. |
| 7,052,472 B1 | 5/2006 | Miller et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,076,300 B1 | 7/2006 | Kroll et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,096,064 B2 | 8/2006 | Deno et al. |
| 7,098,803 B2 | 8/2006 | Mann et al. |
| 7,103,412 B1 | 9/2006 | Kroll |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |
| 7,136,689 B2 | 11/2006 | Shults et al. |
| 7,142,911 B2 | 11/2006 | Boileau et al. |
| 7,153,265 B2 | 12/2006 | Vachon |
| 7,167,818 B2 | 1/2007 | Brown |
| 7,171,274 B2 | 1/2007 | Starkweather et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,220,387 B2 | 5/2007 | Flaherty et al. |
| 7,225,535 B2 | 6/2007 | Feldman et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,673 B2 | 8/2007 | Racchini et al. |
| 7,267,665 B2 | 9/2007 | Steil et al. |
| 7,272,436 B2 | 9/2007 | Gill et al. |
| 7,276,029 B2 | 10/2007 | Goode, Jr. et al. |
| 7,278,983 B2 | 10/2007 | Ireland et al. |
| 7,295,867 B2 | 11/2007 | Berner et al. |
| 7,297,114 B2 | 11/2007 | Gill et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |

(56) References Cited

U.S. PATENT DOCUMENTS

| | | |
|---|---|---|
| 7,366,556 B2 | 4/2008 | Brister et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,491,303 B2 | 2/2009 | Sakata et al. |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,502,644 B2 | 3/2009 | Gill et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,524,287 B2 | 4/2009 | Bharmi |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,577,469 B1 | 8/2009 | Aronowitz et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,620,438 B2 | 11/2009 | He |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,659,823 B1 | 2/2010 | Killian et al. |
| 7,668,596 B2 | 2/2010 | Von Arx et al. |
| 7,699,775 B2 | 4/2010 | Desai et al. |
| 7,699,964 B2 | 4/2010 | Feldman et al. |
| 7,711,493 B2 | 5/2010 | Bartkowiak et al. |
| 7,736,310 B2 | 6/2010 | Taub et al. |
| 7,741,734 B2 | 6/2010 | Joannopoulos et al. |
| 7,751,864 B2 | 7/2010 | Buck, Jr. |
| 7,766,829 B2 | 8/2010 | Sloan et al. |
| 7,771,352 B2 | 8/2010 | Shults et al. |
| 7,774,145 B2 | 8/2010 | Bruaker et al. |
| 7,778,680 B2 | 8/2010 | Goode, Jr. et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,826,981 B2 | 11/2010 | Goode, Jr. et al. |
| 7,831,310 B2 | 11/2010 | Lebel et al. |
| 7,842,174 B2 | 11/2010 | Zhou et al. |
| 7,857,760 B2 | 12/2010 | Brister et al. |
| 7,860,574 B2 | 12/2010 | Von Arx et al. |
| 7,866,026 B1 | 1/2011 | Wang et al. |
| 7,882,611 B2 | 2/2011 | Shah et al. |
| 7,885,697 B2 | 2/2011 | Brister et al. |
| 7,889,069 B2 | 2/2011 | Fifolt et al. |
| 7,899,511 B2 | 3/2011 | Shults et al. |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,920,906 B2 | 4/2011 | Goode et al. |
| 7,938,797 B2 | 5/2011 | Estes |
| 7,946,984 B2 | 5/2011 | Brister et al. |
| 7,955,258 B2 | 6/2011 | Goscha et al. |
| 7,970,448 B2 | 6/2011 | Shults et al. |
| 7,974,672 B2 | 7/2011 | Shults et al. |
| 7,999,674 B2 | 8/2011 | Kamen |
| 8,060,173 B2 | 11/2011 | Goode, Jr. et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,116,837 B2 | 2/2012 | Huang |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,140,312 B2 | 3/2012 | Hayter et al. |
| 8,150,321 B2 | 4/2012 | Winter et al. |
| 8,150,516 B2 | 4/2012 | Levine et al. |
| 8,160,900 B2 | 4/2012 | Taub et al. |
| 8,170,803 B2 | 5/2012 | Kamath et al. |
| 8,179,266 B2 | 5/2012 | Hermle |
| 8,211,016 B2 | 7/2012 | Budiman |
| 8,216,137 B2 | 7/2012 | Budiman |
| 8,216,138 B1 | 7/2012 | McGarraugh et al. |
| 8,224,415 B2 | 7/2012 | Budiman et al. |
| 8,239,166 B2 | 8/2012 | Hayter et al. |
| 8,255,026 B1 | 8/2012 | Al-Ali |
| 8,282,549 B2 | 10/2012 | Brauker et al. |
| 8,376,945 B2 | 2/2013 | Hayter et al. |
| 8,396,670 B2 | 3/2013 | St-Pierre |
| 8,444,560 B2 | 5/2013 | Hayter et al. |
| 8,457,703 B2 | 6/2013 | Al-Ali |
| 8,484,005 B2 | 7/2013 | Hayter et al. |
| 8,532,935 B2 | 9/2013 | Budiman |
| 8,543,354 B2 | 9/2013 | Luo et al. |
| 8,571,808 B2 | 10/2013 | Hayter |
| 8,608,923 B2 | 12/2013 | Zhou et al. |
| 8,612,163 B2 | 12/2013 | Hayter et al. |
| 8,657,746 B2 | 2/2014 | Roy |
| 8,682,615 B2 | 3/2014 | Hayter et al. |
| 9,060,719 B2 | 6/2015 | Hayter et al. |
| 9,113,828 B2 | 8/2015 | Budiman |
| 9,241,631 B2 | 1/2016 | Valdes et al. |
| 9,398,872 B2 | 7/2016 | Hayter et al. |
| 9,408,566 B2 | 8/2016 | Hayter et al. |
| 9,483,608 B2 | 11/2016 | Hayter et al. |
| 9,504,471 B2 | 11/2016 | Lee et al. |
| 9,558,325 B2 | 1/2017 | Hayter et al. |
| 9,801,577 B2 | 10/2017 | Budiman et al. |
| 9,808,574 B2 | 11/2017 | Yodfat et al. |
| 10,820,842 B2 | 11/2020 | Harper |
| 10,827,954 B2 | 11/2020 | Hoss et al. |
| 10,874,338 B2 | 12/2020 | Stafford |
| 10,881,341 B1 | 1/2021 | Curry et al. |

(56) References Cited

U.S. PATENT DOCUMENTS

| | | |
|---|---|---|
| 10,945,647 B2 | 3/2021 | Mazza |
| 10,945,649 B2 | 3/2021 | Lee et al. |
| 10,952,653 B2 | 3/2021 | Harper |
| 10,959,654 B2 | 3/2021 | Curry et al. |
| 10,966,644 B2 | 4/2021 | Stafford |
| 10,973,443 B2 | 4/2021 | Funderburk et al. |
| 11,000,213 B2 | 5/2021 | Kamath et al. |
| 11,000,216 B2 | 5/2021 | Curry et al. |
| 11,013,440 B2 | 5/2021 | Lee et al. |
| 11,020,031 B1 | 6/2021 | Simpson et al. |
| 11,064,917 B2 | 7/2021 | Simpson et al. |
| 11,141,084 B2 | 10/2021 | Funderburk et al. |
| 2001/0041831 A1 | 11/2001 | Starkweather et al. |
| 2002/0010390 A1 | 1/2002 | Guice et al. |
| 2002/0016534 A1 | 2/2002 | Trepagnier et al. |
| 2002/0019022 A1 | 2/2002 | Dunn et al. |
| 2002/0042090 A1 | 4/2002 | Heller et al. |
| 2002/0043651 A1 | 4/2002 | Darrow et al. |
| 2002/0065454 A1 | 5/2002 | Lebel et al. |
| 2002/0068860 A1 | 6/2002 | Clark |
| 2002/0072784 A1 | 6/2002 | Sheppard et al. |
| 2002/0103499 A1 | 8/2002 | Perez et al. |
| 2002/0106709 A1 | 8/2002 | Potts et al. |
| 2002/0120186 A1 | 8/2002 | Keimel |
| 2002/0128594 A1 | 9/2002 | Das et al. |
| 2002/0143266 A1 | 10/2002 | Bock |
| 2002/0143372 A1 | 10/2002 | Snell et al. |
| 2002/0156355 A1 | 10/2002 | Gough |
| 2002/0161288 A1 | 10/2002 | Shin et al. |
| 2002/0169635 A1 | 11/2002 | Shillingburg |
| 2002/0177764 A1 | 11/2002 | Sohrab |
| 2002/0193679 A1 | 12/2002 | Malave et al. |
| 2003/0003524 A1 | 1/2003 | Taniike et al. |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0065308 A1 | 4/2003 | Lebel et al. |
| 2003/0076082 A1 | 4/2003 | Morgan et al. |
| 2003/0100821 A1 | 5/2003 | Heller et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0235817 A1 | 12/2003 | Bartkowiak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0018486 A1 | 1/2004 | Dunn et al. |
| 2004/0022438 A1 | 2/2004 | Hibbard |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0077962 A1 | 4/2004 | Kroll |
| 2004/0078065 A1 | 4/2004 | Kroll |
| 2004/0093167 A1 | 5/2004 | Braig et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0127777 A1 | 7/2004 | Ruchti et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0138716 A1 | 7/2004 | Kon et al. |
| 2004/0142403 A1 | 7/2004 | Hetzel et al. |
| 2004/0146909 A1 | 7/2004 | Duong et al. |
| 2004/0152622 A1 | 8/2004 | Keith et al. |
| 2004/0162678 A1 | 8/2004 | Hetzel et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0208780 A1 | 10/2004 | Faries, Jr. et al. |
| 2004/0225338 A1 | 11/2004 | Lebel et al. |
| 2004/0236200 A1 | 11/2004 | Say et al. |
| 2004/0244151 A1 | 12/2004 | Sakata et al. |
| 2004/0249253 A1 | 12/2004 | Racchini et al. |
| 2004/0249420 A1 | 12/2004 | Olson et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0049473 A1 | 3/2005 | Desai et al. |
| 2005/0059871 A1 | 3/2005 | Gough et al. |
| 2005/0069892 A1 | 3/2005 | Iyengar et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0115832 A1 | 6/2005 | Simpson et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0143636 A1 | 6/2005 | Zhang et al. |
| 2005/0151976 A1 | 7/2005 | Toma |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0196821 A1 | 9/2005 | Monfre et al. |
| 2005/0199494 A1 | 9/2005 | Say et al. |
| 2005/0203360 A1 | 9/2005 | Brauker et al. |
| 2005/0214892 A1 | 9/2005 | Kovatchev et al. |
| 2005/0215871 A1 | 9/2005 | Feldman et al. |
| 2005/0239154 A1 | 10/2005 | Feldman et al. |

(56) References Cited

U.S. PATENT DOCUMENTS

| | | |
|---|---|---|
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0277164 A1 | 12/2005 | Drucker et al. |
| 2005/0277912 A1 | 12/2005 | John |
| 2005/0287620 A1 | 12/2005 | Heller et al. |
| 2005/0288725 A1 | 12/2005 | Hettrick et al. |
| 2006/0001538 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0091006 A1 | 5/2006 | Wang et al. |
| 2006/0094944 A1 | 5/2006 | Chuang |
| 2006/0094945 A1 | 5/2006 | Barman et al. |
| 2006/0142651 A1 | 6/2006 | Brister et al. |
| 2006/0155180 A1 | 7/2006 | Brister et al. |
| 2006/0166629 A1 | 7/2006 | Reggiardo |
| 2006/0167365 A1 | 7/2006 | Bharmi |
| 2006/0167517 A1 | 7/2006 | Gill et al. |
| 2006/0167518 A1 | 7/2006 | Gill et al. |
| 2006/0167519 A1 | 7/2006 | Gill et al. |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee |
| 2006/0222566 A1 | 10/2006 | Brauker et al. |
| 2006/0224109 A1 | 10/2006 | Steil et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247685 A1 | 11/2006 | Bharmi |
| 2006/0247710 A1 | 11/2006 | Goetz et al. |
| 2006/0247985 A1 | 11/2006 | Liamos et al. |
| 2006/0258929 A1 | 11/2006 | Goode, Jr. et al. |
| 2006/0258959 A1 | 11/2006 | Sode |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2006/0293576 A1 | 12/2006 | Van Antwerp et al. |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0038044 A1 | 2/2007 | Dobbles et al. |
| 2007/0055799 A1 | 3/2007 | Koehler et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0118030 A1 | 5/2007 | Bruce et al. |
| 2007/0118405 A1 | 5/2007 | Campbell et al. |
| 2007/0124002 A1 | 5/2007 | Estes et al. |
| 2007/0129621 A1 | 6/2007 | Kellogg et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0213657 A1 | 9/2007 | Jennewine et al. |
| 2007/0227911 A1 | 10/2007 | Wang et al. |
| 2007/0232877 A1 | 10/2007 | He |
| 2007/0232878 A1 | 10/2007 | Kovatchev et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255321 A1 | 11/2007 | Gerber et al. |
| 2007/0255531 A1 | 11/2007 | Drew |
| 2007/0258395 A1 | 11/2007 | Jollota et al. |
| 2007/0270672 A1 | 11/2007 | Hayter |
| 2007/0285238 A1 | 12/2007 | Batra |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0012701 A1 | 1/2008 | Kass et al. |
| 2008/0017522 A1 | 1/2008 | Heller et al. |
| 2008/0018433 A1 | 1/2008 | Pitt-Pladdy |
| 2008/0021666 A1 | 1/2008 | Goode, Jr. et al. |
| 2008/0021972 A1 | 1/2008 | Huelskamp et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0064943 A1 | 3/2008 | Talbot et al. |
| 2008/0066305 A1 | 3/2008 | Wang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0087544 A1 | 4/2008 | Zhou et al. |
| 2008/0097289 A1 | 4/2008 | Steil et al. |

(56) References Cited

U.S. PATENT DOCUMENTS

| | | |
|---|---|---|
| 2008/0102441 A1 | 5/2008 | Chen et al. |
| 2008/0108942 A1 | 5/2008 | Brister et al. |
| 2008/0119703 A1 | 5/2008 | Brister et al. |
| 2008/0119705 A1 | 5/2008 | Patel et al. |
| 2008/0119708 A1 | 5/2008 | Budiman |
| 2008/0139910 A1 | 6/2008 | Mastrototaro et al. |
| 2008/0148873 A1 | 6/2008 | Wang |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234943 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0275313 A1 | 11/2008 | Brister et al. |
| 2008/0278332 A1 | 11/2008 | Fennel et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054748 A1 | 2/2009 | Feldman et al. |
| 2009/0054749 A1 | 2/2009 | He |
| 2009/0054753 A1 | 2/2009 | Robinson et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0069649 A1 | 3/2009 | Budiman |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0099436 A1 | 4/2009 | Brister et al. |
| 2009/0102678 A1 | 4/2009 | Mazza et al. |
| 2009/0105554 A1 | 4/2009 | Stahmann et al. |
| 2009/0105570 A1 | 4/2009 | Sloan et al. |
| 2009/0105636 A1 | 4/2009 | Hayter et al. |
| 2009/0112478 A1 | 4/2009 | Mueller, Jr. et al. |
| 2009/0112626 A1 | 4/2009 | Talbot et al. |
| 2009/0118589 A1 | 5/2009 | Ueshima et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143725 A1 | 6/2009 | Peyser et al. |
| 2009/0149728 A1 | 6/2009 | Van Antwerp et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163789 A1 | 6/2009 | Say et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0182517 A1 | 7/2009 | Gandhi et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |

(56) References Cited

U.S. PATENT DOCUMENTS

| | | |
|---|---|---|
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0257911 A1 | 10/2009 | Thomas et al. |
| 2009/0267765 A1 | 10/2009 | Greene et al. |
| 2009/0281407 A1 | 11/2009 | Budiman |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0294277 A1 | 12/2009 | Thomas et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0064764 A1 | 3/2010 | Hayter et al. |
| 2010/0081906 A1 | 4/2010 | Hayter et al. |
| 2010/0081909 A1 | 4/2010 | Budiman et al. |
| 2010/0081953 A1 | 4/2010 | Syeda-Mahmood et al. |
| 2010/0121167 A1 | 5/2010 | McGarraugh et al. |
| 2010/0141656 A1 | 6/2010 | Krieftewirth |
| 2010/0145377 A1 | 6/2010 | Lai et al. |
| 2010/0152561 A1 | 6/2010 | Goodnow et al. |
| 2010/0160759 A1 | 6/2010 | Celentano et al. |
| 2010/0160761 A1 | 6/2010 | Say et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0190435 A1 | 7/2010 | Cook et al. |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213057 A1 | 8/2010 | Feldman et al. |
| 2010/0230285 A1* | 9/2010 | Hoss ................. A61B 5/14865 204/415 |
| 2010/0234710 A1 | 9/2010 | Budiman et al. |
| 2010/0261987 A1 | 10/2010 | Kamath et al. |
| 2010/0265073 A1 | 10/2010 | Harper et al. |
| 2010/0274515 A1 | 10/2010 | Hoss et al. |
| 2010/0277342 A1 | 11/2010 | Sicurello et al. |
| 2010/0280441 A1 | 11/2010 | Willinska et al. |
| 2010/0280782 A1 | 11/2010 | Harper et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0326842 A1 | 12/2010 | Mazza et al. |
| 2011/0004276 A1 | 1/2011 | Blair et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0029247 A1 | 2/2011 | Kalathil |
| 2011/0036714 A1 | 2/2011 | Zhou et al. |
| 2011/0040163 A1 | 2/2011 | Telson et al. |
| 2011/0060530 A1 | 3/2011 | Fennell |
| 2011/0077490 A1 | 3/2011 | Simpson et al. |
| 2011/0077494 A1 | 3/2011 | Doniger et al. |
| 2011/0081726 A1 | 4/2011 | Berman et al. |
| 2011/0082484 A1 | 4/2011 | Saravia et al. |
| 2011/0105873 A1 | 5/2011 | Feldman et al. |
| 2011/0106126 A1 | 5/2011 | Love et al. |
| 2011/0112696 A1 | 5/2011 | Yodfat et al. |
| 2011/0148905 A1 | 6/2011 | Simmons et al. |
| 2011/0152637 A1 | 6/2011 | Kateraas et al. |
| 2011/0184268 A1 | 7/2011 | Taub |
| 2011/0190603 A1 | 8/2011 | Stafford |
| 2011/0191044 A1 | 8/2011 | Stafford |
| 2011/0193704 A1 | 8/2011 | Harper et al. |
| 2011/0208027 A1 | 8/2011 | Wagner et al. |
| 2011/0208155 A1 | 8/2011 | Palerm et al. |
| 2011/0213225 A1 | 9/2011 | Bernstein et al. |
| 2011/0224523 A1 | 9/2011 | Budiman |
| 2011/0257495 A1 | 10/2011 | Hoss et al. |
| 2011/0257895 A1 | 10/2011 | Brauker et al. |
| 2011/0263958 A1 | 10/2011 | Brauker et al. |
| 2011/0288574 A1 | 11/2011 | Curry et al. |
| 2011/0319729 A1 | 12/2011 | Donnay et al. |
| 2011/0320130 A1 | 12/2011 | Valdes et al. |
| 2011/0320167 A1 | 12/2011 | Budiman |
| 2012/0010642 A1 | 1/2012 | Lee et al. |
| 2012/0078071 A1 | 3/2012 | Bohm et al. |
| 2012/0108931 A1 | 5/2012 | Taub |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0209099 A1 | 8/2012 | Ljuhs et al. |
| 2012/0215462 A1 | 8/2012 | Goode et al. |
| 2012/0245447 A1 | 9/2012 | Karan et al. |
| 2012/0277565 A1 | 11/2012 | Budiman |
| 2012/0283542 A1 | 11/2012 | McGarraugh |
| 2012/0318670 A1 | 12/2012 | Karinka et al. |
| 2013/0035575 A1 | 2/2013 | Mayou et al. |
| 2013/0137953 A1 | 5/2013 | Harper et al. |
| 2013/0184547 A1 | 7/2013 | Taub et al. |
| 2013/0231541 A1 | 9/2013 | Hayter et al. |
| 2013/0324823 A1 | 12/2013 | Koski et al. |
| 2014/0005499 A1 | 1/2014 | Catt et al. |
| 2014/0046160 A1 | 2/2014 | Terashima et al. |
| 2014/0088392 A1 | 3/2014 | Bernstein et al. |
| 2014/0121480 A1 | 5/2014 | Budiman et al. |
| 2014/0121488 A1 | 5/2014 | Budiman |
| 2014/0221966 A1 | 8/2014 | Buckingham et al. |
| 2015/0005601 A1 | 1/2015 | Hoss et al. |
| 2015/0216456 A1 | 8/2015 | Budiman |
| 2015/0241407 A1 | 8/2015 | Ou et al. |
| 2015/0366510 A1 | 12/2015 | Budiman |
| 2016/0022221 A1 | 1/2016 | Ou et al. |
| 2016/0302701 A1 | 10/2016 | Bhavaraju et al. |
| 2017/0112531 A1 | 4/2017 | Schoonmaker et al. |
| 2019/0274598 A1 | 9/2019 | Scott et al. |
| 2022/0142518 A1 | 5/2022 | Budiman et al. |

FOREIGN PATENT DOCUMENTS

| | | |
|---|---|---|
| EP | 0320109 | 6/1989 |
| EP | 0353328 | 2/1990 |
| EP | 0390390 | 10/1990 |
| EP | 0396788 | 11/1990 |
| EP | 0472411 | 2/1992 |
| EP | 0286118 | 1/1995 |
| EP | 0867146 | 9/1998 |
| EP | 1048264 | 11/2000 |
| EP | 1391728 | 2/2004 |
| EP | 1419731 | 5/2004 |
| EP | 0939602 | 9/2004 |
| EP | 1850909 | 4/2010 |
| EP | 1677668 | 7/2010 |
| EP | 1 413 879 | 1/2012 |
| EP | 3575796 | 12/2019 |

(56) References Cited

FOREIGN PATENT DOCUMENTS

| WO | WO-1996/025089 | 8/1996 |
|---|---|---|
| WO | WO-1996/035370 | 11/1996 |
| WO | WO-1997/015227 | 5/1997 |
| WO | WO-1998/035053 | 8/1998 |
| WO | WO-1999/056613 | 11/1999 |
| WO | WO-00/49941 | 8/2000 |
| WO | WO-2000/049940 | 8/2000 |
| WO | WO-2000/059370 | 10/2000 |
| WO | WO-2000/074753 | 12/2000 |
| WO | WO-2001/052935 | 7/2001 |
| WO | WO-2001/054753 | 8/2001 |
| WO | WO-2002/016905 | 2/2002 |
| WO | WO 02/058537 | 8/2002 |
| WO | WO-03/012422 | 2/2003 |
| WO | WO-03/032411 | 4/2003 |
| WO | WO-2003/076893 | 9/2003 |
| WO | WO-2003/082091 | 10/2003 |
| WO | WO-03/094714 | 11/2003 |
| WO | WO-2004/060455 | 7/2004 |
| WO | WO-2005/010756 | 2/2005 |
| WO | WO-2005/011489 | 2/2005 |
| WO | WO-2005/065542 | 7/2005 |
| WO | WO-2005/070287 | 8/2005 |
| WO | WO-2006/024671 | 3/2006 |
| WO | WO 2006/026741 | 3/2006 |
| WO | WO-2006/081336 | 8/2006 |
| WO | WO-2007/097754 | 8/2007 |
| WO | WO-2008/021913 | 2/2008 |
| WO | WO-2008/086541 | 7/2008 |
| WO | WO-2010/022387 | 2/2010 |
| WO | WO-2010/099507 | 9/2010 |
| WO | WO-2011/011643 | 1/2011 |
| WO | WO-2012/142502 | 10/2012 |

OTHER PUBLICATIONS

Bard, A. J., et al., Electrochemical Methods, Fundamentals and Applications, John Wiley & Sons, pp. 174-175.
Chen, T., et al., "In Situ Assembled Mass-Transport Controlling Micromembranes and Their Application in Implanted Amperometric Glucose Sensors", Analytical Chemistry, vol. 72, No. 16, 2000, pp. 3757-3763.
Chen, T., et al., In vivo Glucose Monitoring with Miniature "Wired" Glucose Oxidase Electrodes, Analytical Sciences, vol. 17, 2001, pp. i297-i300.
Chen, X., et al., "Glucose microbiosensor based on alumina sol gel matrix. electropolymerized composite membrane", Biosensors and Bioelectronics, 2002, 9 pages.
Chung, T. D., "In vitro Evaluation of the Continuous Monitoring Glucose Sensors with Perfluorinated Tetrafluoroethylene Coatings", Bull. Korean Chem. Soc., vol. 24, No. 4, 2003, pp. 514-516.
Cunningham, D. D., et al., "In Vivo Glucose Sensing", Chemical Analysis: A Series of Monographs on Analytical Chemistry and Its Applications, vol. 174, John Wiley & Sons, Inc., 2010, 466 pages.
Freestyle Navigator, Continuous Glucose Monitoring System, User's Guide, 2008, Abbott, 195 pages.
Guardian® REAL-Time, Continuous Glucose Monitoring System, User Guide, Medtronic MiniMed, Inc., 2006, 181 pages.
Guardian® RT, Continuous Glucose Monitoring System, REF MMT-7900, User Guide, Medtronic MiniMed, 2005, 128 pages.
Heller, A., "Implanted Electrochemical Glucose Sensors for the Management of Diabetes", Annual Review of Biomedical Engineering, vol. 1, 1999, pp. 153-175.
Heller, A., et al., "Electrochemical Glucose Sensors and Their Applications in Diabetes Management", Chemical Reviews, 2008, pp. 2482-2505.
Jimenez, C., et al., "Glucose sensor based on an amperometric microelectrode with a photopolymerizable enzyme membrane", Sensors and Actuators B 26-27, 1995, pp. 421-424.
Klonoff, D. C., et al., "Diabetes Technology & Therapeutics", vol. 5, No. 4, 2003, 14 pages.

Moatti-Sirat, D., et al., Evaluating in vitro and in vivo the interference of ascorbate and acetaminophen on glucose detection by a needle-type glucose sensor, Biosensors & Bioelectronics, 7, 1992, pp. 345-349.
Nishida, K., et al., "Development of a ferrocene-mediated needle-type glucose sensor covered with newly designed biocompatible membrane, 2-methacryloyloxyethyl phosphorylcholine-co-n-butyl methacrylate", Medical Progress through Technology, vol. 21, 1995, pp. 91-103.
Rhodes, R. K., et al., "Prediction of Pocket-Portable and Implantable Glucose Enzyme Electrode Performance from Combined Species Permeability and Digital Simulation Analysis", Analytical Chemistry, vol. 66, No. 9, 1994. pp. 1520-1529.
Summary of Safety and Effectiveness Data, FreeStyle Navigator® Continuous Glucose Monitoring System, Abbott Diabetes Care, 2008, 27 pages.
Tierney, M. J., et al., "Effect of Acetaminophen on the Accuracy of Glucose Measurements Obtained with the GlucoWatch Biographer", Diabetes Technology & Therapeutics, vol. 2, No. 2, 2000, pp. 199-208.
Yang, S., et al., "Glucose Biosensors Based on Oxygen Electrode with Sandwich-Type Membranes", Annals of Biomedical Engineering, vol. 23, 1995, pp. 833-839.
Yang, S., et al., "Glucose Biosensors with Enzyme Entrapped in Polymer Coating", Original Research, Biomedical Instrumentation & Technology, 1995, pp. 125-133.
U.S. Appl. No. 16/256,855, filed Nov. 22, 2022 Response to Final Office Action with Request for Continued Examination and Terminal Disclaimer.
U.S. Appl. No. 16/256,855, filed Oct. 27, 2022 Final Office Action.
U.S. Appl. No. 16/256,855, filed Oct. 12, 2022 Response to Non-Final Office Action.
Abel, et al., "Biosensors for in vivo glucose measurement: can we cross the experimental stage", Biosensors and Bioelectronics, 17:1059-1070 (2002).
Alcock, et al., "Continuous Analyte Monitoring to Aid Clinical Practice", IEEE Engineering in Medicine and Biology, pp. 319-325 (1994).
Bequette, "Continuous Glucose Monitoring: Real Time Algorithms for Calibration, Filtering, and Alarms", Journal of Diabetes Science and Technology, 4(2):404-418 (2010).
Cengiz, et al., "A Tale of Two Compartments: Interstitial Versus Blood Glucose Monitoring", Diabetes Technology & Therapeutics, 11(1):S-11-S16 (2009).
Chen, et al., "Defining the Period of Recovery of the Glucose Concentration after Its Local Perturbation by the Implantation of a Miniature Sensor", Clin Chem Lab Med, 40(8):786-789 (2002).
De Block, et al., "Minimally-Invasive and Non-Invasive Continuous Glucose Monitoring Systems: Indications, Advantages, Limitations and Clinical Aspects", Current Diabetes Reviews, 4:159-168 (2008).
Facchinetti, et al., "Enhanced Accuracy of Continuous Glucose Monitoring by Online Extended Kalman Filtering", Diabetes Technology & Therapeutics, 12(5):353-363 (2010).
Gerritsen, et al., "Subcutaneously implantable glucose sensors in patients with diabetes mellitus; still many problems", Dutch Journal of Medicine, 146(28):1313-1316 (2002) (with English Machine Translation).
Heinemann, "Continuous Glucose Monitoring by Means of the Microdialysis Technique: Underlying Fundamental Aspects", Diabetes Technology & Therapeutics, 5(4):545-561 (2003).
Knobbe, et al., "The Extended Kalman Filter for Continuous Glucose Monitoring", Diabetes Technology & Therapeutics, 7(1):15-27 (2005).
Koudelka, et al., "In-vivo Behaviour of Hypodermically Implanted Microfabricated Glucose Sensors", Biosensors & Bioelectronics, 6:31-36 (1991).
Koudelka-Hep, "Electrochemical Sensors for in vivo Glucose Sensing", Biosensors in the Body: Continuous in vivo Monitoring, pp. 57-77 (1997).
Kvist, et al., "Recent Advances in Continuous Glucose Monitoring: Biocompatibility of Glucose Sensors for Implantation in Subcutis", Journal of Diabetes Science and Technology, 1(5):746-752 (2007).

(56) References Cited

OTHER PUBLICATIONS

Ming Li, et al., "Implantable Electrochemical Sensors for Biomedical and Clinical Applications: Progress, Problems, and Future Possibilities", Current Medicinal Chemistry, 14:937-951 (2007).
Onuki, et al., "A Review of the Biocompatibility of Implantable Devices: Current Challenges to Overcome Foreign Body Response", Journal of Diabetes Science and Technology, 2(6):1003-1015 (2008).
Palerm, et al., "Hypoglycemia Prediction and Detection Using Optimal Estimation", Diabetes Technology & Therapeutics, 7(1):3-14 (2005).
Poitout, et al., "Calibration in dogs of a subcutaneous miniaturized glucose sensor using a glucose meter for blood glucose determination", Biosensors & Bioelectronics, 7:587-592 (1992).
Rebrin, et al., "Subcutaneous glucose predicts plasma glucose independent of insulin: implications for continuous monitoring", American Journal of Physiology-Endocrinology and Metabolism, 277(3):E561-E571 (1999).
Renard, "Implantable glucose sensors for diabetes monitoring", Min Invas Ther & Allied Technol, 13(2):78-86 (2004).
Robert, "Continuous Monitoring of Blood Glucose", Horm Res 57(suppl 1):81-84 (2002).
Schlosser, et al., "Biocompatibility of Active Implantable Devices", Biosensors in the Body: Continuous in vivo Monitoring, pp. 139-170 (1997).
Schmidt, et al., "Calibration of a wearable glucose sensor", The International Journal of Artificial Organs, 15(1):55-61 (1992).
Voskerician, et al., "Sensor Biocompatibility and Biofouling in Real-Time Monitoring", Wiley Encyclopedia of Biomedical Engineering, (John Wiley & Sons, Inc.), pp. 1-19 (2006).
Ward, "A Review of the Foreign-body Response to Subcutaneously-implanted Devices: The Role of Macrophages and Cytokines in Biofouling and Fibrosis", Journal of Diabetes Science and Technology, 2(5):768-777 (2008).
Ward, et al., "A new amperometric glucose microsensor: in vitro and short-term in vivo evaluation", Biosensors & Bioelectronics, 17:181-189 (2002).
U.S. Appl. No. 16/256,855 (US 2019-0150802 A1), filed Jan. 24, 2019 (May 23, 2019).
U.S. Appl. No. 15/789,949 (U.S. Pat. No. 10,188,334), filed Oct. 20, 2017 (Jan. 29, 2019).
U.S. Appl. No. 15/616,916 (U.S. Pat. No. 9,801,577), filed Jun. 7, 2017 (Oct. 31, 2017).
U.S. Appl. No. 14/066,650 (U.S. Pat. No. 9,675,290), filed Oct. 29, 2013 (Jun. 13, 2017).
U.S. Appl. No. 16/256,855, Jul. 12, 2022 Non-Final Office Action.
U.S. Appl. No. 16/256,855, Jun. 23, 2022 TrackOne Request Granted.
U.S. Appl. No. 16/256,855, Jun. 1, 2022 Response to Final Office Action with Request for Continued Examination (RCE) & TrackOne Request.
U.S. Appl. No. 16/256,855, Apr. 1, 2022 Final Office Action.
U.S. Appl. No. 16/256,855, Mar. 7, 2022 Response to Non-Final Office Action.
U.S. Appl. No. 16/256,855, Jan. 7, 2022 Non-Final Office Action.
U.S. Appl. No. 16/256,855, Nov. 22, 2021 Response to Non-Final Office Action.
U.S. Appl. No. 16/256,855, Aug. 25, 2021 Non-Final Office Action.
Armour, J. C., et al., "Application of Chronic Intravascular Blood Glucose Sensor in Dogs", Diabetes, vol. 39, 1990, pp. 1519-1526.
Arnold, M. A., et al., "Selectivity Assessment of Noninvasive Glucose Measurements Based on Analysis of Multivariate Calibration Vectors", Journal of Diabetes Science and Technology, vol. 1, No. 4, 2007, pp. 454-462.
Bennion, N., et al., "Alternate Site Glucose Testing: A Crossover Design", Diabetes Technology & Therapeutics, vol. 4, No. 1, 2002, pp. 25-33.
Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.

Boyne, M. S., et al., "Timing of Changes in Interstitial and Venous Blood Glucose Measured With a Continuous Subcutaneous Glucose Sensor", Diabetes, vol. 52, Nov. 2003, pp. 2790-2794.
Bremer, T. M., et al., "Benchmark Data from the Literature for Evaluation of New Glucose Sensing Technologies", Diabetes Technology & Therapeutics vol. 3 No. 3, 2001, pp. 409-418.
Brooks, S. L., et al., "Development of an On-Line Glucose Sensor for Fermentation Monitoring", Biosensors, vol. 3, 1987/88, pp. 45-56.
Cass, A. E., et al., "Ferrocene-Medicated Enzyme Electrode for Amperometric Determination of Glucose", Analytical Chemistry, vol. 56, No. 4, 1984, 667-671.
Cheyne, E. H., et al., Performance of a Continuous Glucose Monitoring System During Controlled Hypoglycaemia in Healthy Volunteers, Diabetes Technology & Therapeutics, vol. 4, No. 5, 2002, pp. 607-613.
Choleau, C., et al., "Calibration of a Subcutaneous Amperometric Glucose Sensor Implanted for 7 Days in Diabetic Patients Part 2. Superiority of the One-Point Calibration Method", Biosensors and Bioelectronics, vol. 17, No. 8, 2002, pp. 647-654.
Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.
Diabetes Control and Complications Trial Research Group, "The Effect of Intensive Treatment of Diabetes on the Development and Progression of Long-Term Complications in Insulin-Dependent Diabetes Mellitus," New England J. Med. vol. 329, 1993, pp. 977-986.
Eren-Oruklu, M., et al., "Estimation of Future Glucose Concentrations with Subject-Specific Recursive Linear Models", Diabetes Technology & Therapeutics vol. 11(4), 2009, pp. 243-253.
Feldman, B., et al., "A Continuous Glucose Sensor Based on Wired Enzyme™ Technology Results from a 3-Day Trial in Patients with Type 1 Diabetes", Diabetes Technology & Therapeutics, vol. 5, No. 5, 2003, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
Georgescu, B., et al., "Real-Time Multimodel Tracking of Myocardium in Echocardiography Using Robust Information Fusion", Medical Image Computing and Computer-Assisted Intervention, 2004, pp. 777-785.
Goldman, J. M., et al., "Masimo Signal Extraction Pulse Oximetry", Journal of Clinical Monitoring and Computing, vol. 16, No. 7, 2000, pp. 475-483.
Guerci, B., et al., "Clinical Performance of CGMS in Type 1 Diabetic Patients Treated by Continuous Subcutaneous Insulin Infusion Using Insulin Analogs", Diabetes Care, vol. 26, 2003, pp. 582-589.
Hovorka, R., et al., "Nonlinear Model Predictive Control of Glucose Concentration in Subjects with Type 1 Diabetes", Physiological Measurement, vol. 55, Jul. 2004, pp. 905-920.
Isermann, R., "Supervision, Fault-Detection and Fault-Diagnosis Methods—an Introduction", Control Engineering Practice, vol. 5, No. 5, 1997, pp. 639-652.
Isermann, R., et al., "Trends in the Application of Model-Based Fault Detection and Diagnosis of Technical Processes", Control Engineering Practice, vol. 5, No. 5, 1997, pp. 709-719.
Johnson, P. C., "Peripheral Circulation", John Wiley & Sons, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", Diabetes Care, vol. 24, No. 7, 2001, pp. 1303-1304.
Kaplan, S. M., "Wiley Electrical and Electronics Engineering Dictionary", IEEE Press, 2004, pp. 141, 142, 548, 549.
Kovatchev, B. P., et al., "Evaluating the Accuracy of Continuous Glucose-Monitoring Sensors", Diabetes Care, vol. 27, No. 8, 2004, pp. 1922-1928.

(56) References Cited

OTHER PUBLICATIONS

Kovatchev, B. P., et al., "Graphical and Numerical Evaluation of Continuous Glucose Sensing Time Lag", Diabetes Technology & Therapeutics, vol. 11, No. 3, Feb. 2009, pp. 139-143.
Kuure-Kinsey, M., et al., "A Dual-Rate Kalman Filter for Continuous Glucose Monitoring", Proceedings of the 28th IEEE, EMBS Annual International Conference, New York City, 2006, pp. 63-66.
Lodwig, V., et al., "Continuous Glucose Monitoring with Glucose Sensors: Calibration and Assessment Criteria", Diabetes Technology & Therapeutics vol. 5 No. 4 2003, pp. 573-587.
Lortz, J., et al., "What is Bluetooth? We Explain the Newest Short-Range Connectivity Technology", Smart Computing Learning Series, Wireless Computing, vol. 8, Issue 5, 2002, pp. 72-74.
Maher, "A Method for Extrapolation of Missing Digital Audio Data", Preprints of Papers Presented at the AES Convention, 1993, pp. 1-19.
Maher, "Audio Enhancement using Nonlinear Time-Frequency Filtering", AES 26th International Conference, 2005, pp. 1-9.
Malin, S. F., et al., "Noninvasive Prediction of Glucose by Near-Infrared Diffuse Reflectance Spectoscopy", Clinical Chemistry, vol. 45, No. 9, 1999, pp. 1651-1658.
McGarraugh, G., et al., "Glucose Measurements Using Blood Extracted from the Forearm and the Finger", TheraSense, Inc., 2001, 16 Pages.
McGarraugh, G., et al., "Physiological Influences on Off-Finger Glucose Testing", Diabetes Technology & Therapeutics, vol. 3, No. 3, 2001, pp. 367-376.
McKean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.
Morbiducci, U, et al., "Improved Usability of the Minimal Model of Insulin Sensitivity Based on an Automated Approach and Genetic Algorithms for Parameter Estimation", Clinical Science, vol. 112, 2007, pp. 257-263.
Mougiakakou, et al., "A Real Time Simulation Model of Glucose-Insulin Metabolism for Type 1 Diabetes Patients", Proceedings of the 2005 IEEE, 2005, pp. 298-301.
Panteleon, A. E., et al., "The Role of the Independent Variable to Glucose Sensor Calibration", Diabetes Technology & Therapeutics, vol. 5. No. 3, 2003, pp. 401-410.
Parker, R., et al., "Robust H..° Glucose Control in Diabetes Using a Physiological Model", AIChE Journal, vol. 46, No. 12, 2000, pp. 2537-2549.
Pickup, J., et al., "Implantable Glucose Sensors: Choosing the Appropriate Sensing Strategy", Biosensors, vol. 3, 1987/88, pp. 335-346.
Pickup, J., et al., "In Vivo Molecular Sensing in Diabetes Mellitus: An Implantable Glucose Sensor with Direct Electron Transfer", Diabetologia, vol. 32, 1989, pp. 213-217.
Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.
Quinn, C. P., et al., "Kinetics of Glucose Delivery to Subcutaneous Tissue in Rats Measured with 0.3-mm Amperometric Microsensors", The American Physiological Society, 1995, E155-E161.
Rodriguez, N., et al., "Flexible Communication and Control Protocol for Injectable Neuromuscular Interfaces", IEEE Transactions on Biomedical Circuits and Systems, vol. 1, No. 1, 2007. pp. 19-27.
Roe, J. N., et al., "Bloodless Glucose Measurements", Critical Review in Therapeutic Drug Carrier Systems, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.
Sakakida, M., et al., "Ferrocene-Mediated Needle-Type Glucose Sensor Covered with Newly Designed Biocompatible Membrane", Sensors and Actuators B, vol. 13-14, 1993, pp. 319-322.
Salehi, C., et al., "A Telemetry-Instrumentation System for Long-Term Implantable Glucose and Oxygen Sensors", Analytical Letters, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.
Shichiri, M., et al., "Glycaemic Control in Pancreatectomized Dogs with a Wearable Artificial Endocrine Pancreas", Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.
Shichiri, M., et al., "Membrane Design for Extending the Long-Life of an Implantable Glucose Sensor", Diabetes Nutrition and Metabolism, vol. 2, 1989, pp. 309-313.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.
Shichiri, M., et al., "Wearable Artificial Endocrine Pancreas With Needle-Type Glucose Sensor", The Lancet, 1982, pp. 1129-1131.
Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.
Steil, G. M., et al., "Closed-Loop Insulin Delivery—the Path of Physiological Glucose Control", Advanced Drug Delivery Reviews, vol. 56, 2004, pp. 125-144.
Steil, G. M., et al., "Determination of Plasma Glucose During Rapid Glucose Excursions with a Subcutaneous Glucose Sensor", Diabetes Technology & Therapeutics, vol. 5, No. 1, 2003, pp. 27-31.
Sternberg, R., et al., "Study and Development of Multilayer Needle-Type Enzyme-Based Glucose Microsensors", Biosensors, vol. 4, 1988, pp. 27-40.
Thompson, M., et al., "In Vivo Probes: Problems and Perspectives", Clinical Biochemistry, vol. 19, 1986, pp. 255-261.
Turner, A., et al., "Diabetes Mellitus: Biosensors for Research and Management", Biosensors, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.
Velho, G., et al., "Strategies for Calibrating a Subcutaneous Glucose Sensor", Biomedica Biochimica Acta, vol. 48, 1989, pp. 957-964.
Whipple, G., "Low Residual Noise Speech Enhancement Utilizing Time-Frequency", Proceedings of the International Conference on Acoustics, Speech, and Signal Processing, vol. 19, 1994, pp. I5-I8.
Wilson, G. S., et al., "Progress Toward the Development of an Implantable Sensor for Glucose", Clinical Chemistry, vol. 38, No. 9, 1992, pp. 1613-1617.
Wolfe, P. J., et al., "Interpolation of Missing Data Values for Audio Signal Restoration Using a Gabor Regression Model", 2005 IEEE International Conference on Acoustics, Speech, and Signal Processing, vol. 5, 2005, pp. 517-520.
European Patent Application No. 13275272.6, Extended European Search Report dated Mar. 3, 2014.
U.S. Appl. No. 14/066,650, Notice of Allowance dated Feb. 16, 2017.
U.S. Appl. No. 14/066,650, Office Action dated Sep. 23, 2016.
U.S. Appl. No. 14/077,004, Office Action dated Jul. 26, 2016.
U.S. Appl. No. 15/616,916, Notice of Allowance dated Sep. 7, 2017.
U.S. Appl. No. 15/789,949, Notice of Allowance dated Dec. 18, 2018.
U.S. Appl. No. 15/789,949, Office Action dated Dec. 4, 2018.

(56) References Cited

OTHER PUBLICATIONS

U.S. Appl. No. 15/789,949, Office Action dated May 3, 2018.
U.S. Appl. No. 15/796,274, Notice of Allowance dated Jul. 20, 2018.
U.S. Appl. No. 15/334,274, Office Action dated Apr. 25, 2019.
Chen, et al., "A novel fault-tolerant sensor system for sensor drift compensation", Sensors and Actuators, A 147:623-632 (2008).
Gerritsen, et al., "Performance of subcutaneously implanted glucose sensors for continuous monitoring", The Netherlands Journal of Medicine, 54:167-179 (1999).
Kalivas, et al., "Compensation for Drift and Interferences in Multicomponent Analysis", Laboratory for Chemometrics, Department of Chemistry, University of Washington, 38 pages (1982).
Thévenot, et al., "Electrochemical Biosensors: Recommended Definitions and Classification (Technical Report)", Pure Appl. Chem. 71(12):2333-2348 (1999).
U.S. Appl. No. 12/842,013 Office Action mailed Aug. 26, 2015.
U.S. Appl. No. 12/842,013 Office Action mailed Mar. 23, 2016.
U.S. Appl. No. 12/842,013 Office Action mailed Nov. 6, 2014.
Walt, et al., "The chemistry of enzyme and protein immobilization with glutaraldehyde", Trends in Analytical Chemistry, 13(10):425-430 (1994).
Zhang, "Investigations of potentially implantable glucose sensors", University of Kansas, 24 pages (1991).
U.S. Appl. No. 60/687,199, filed Jun. 2, 2005, Ward, et al.
U.S. Appl. No. 61/155,889, filed Feb. 26, 2009, Hoss, et al.
U.S. Appl. No. 18/173,901, May 25, 2023, Non-Final Office Action.
Atanasov, et al., "Implantation of a refillable glucose monitoring-telemetry device", Biosensors & Bioelectronics, 12(7):669-680 (1997).
Bindra, "Development of potentially implantable glucose sensors", The University of Arizona, 227 pages (1990).
Choleau, et al., "Calibration of a subcutaneous amperometric glucose sensor Part 1. Effect of measurement uncertainties on the determination of sensor sensitivity and background current", Biosensors and Bioelectronics, 17:641-646 (2002).
Guardian® Real-Time, Continuous Glucose Monitoring System, User Guide, Medtronic MiniMed, Inc., 184 pages (2006).
Kerner, et al., The function of a hydrogen peroxide-detecting electroenzymatic glucose electrode is markedly impaired in human sub-cutaneous tissue and plasma, Biosensors & Bioelectronics, 8:473-482 (1993).
Koschinsky, et al., "Sensors for glucose monitoring: technical and clinical aspects", Diabetes/Metabolism Research and Reviews, 17:113-123 (2001).
Koschwanez, et al., "In vitro, in vivo and post explantation testing of glucose-detecting biosensors: Current methods and recommendations", Biomaterials, 28:3687-3703 (2007).
Moussy, et al. "Performance of Subcutaneously Implanted Needle-Type Glucose Sensors Employing a Novel Trilayer Coating", Anal. Chem., 65:2072-2077 (1993).
Pickup, et al., "In vivo glucose sensing for diabetes management: progress towards non-invasive monitoring", BMJ, 319, pp. 1-4 (1999).
Pickup, et al., "Responses and calibration of amperometric glucose sensors implanted in the subcutaneous tissue of man", Acta Diabetol, 30:143-148 (1993).
Schmidtke, et al., "Accuracy of the One-Point in Vivo Calibration of "Wired" Glucose Oxidase Electrodes Implanted in Jugular Veins of Rats in Periods of Rapid Rise and Decline of the Glucose Concentration", Anal. Chem., 70:2149-2155 (1998).
Ward, et al., "Rise in background current over time in a subcutaneous glucose sensor in the rabbit: relevance to calibration and accuracy", Biosensors & Bioelectronics, 15:53-61 (2000).
Wilson, et al., "Biosensors for real-time in vivo measurements", Biosensors and Bioelectronics, 20:2388-2403 (2005).
Wisniewski, et al., "Analyte flux through chronically implanted subcutaneous polyamide membranes differs in humans and rats", Am J Physiol Endocrinol Metab, 282:E1316-E1323 (2002).

Abbott receives CE Mark for Freestyle® Libre, a revolutionary glucose monitoring system for people with diabetes, 8 pages (2023).
An Interview with Kevin Sayer, President and CEO of Dexcom, About The New Dexcom G6, 6 pages (2021).
Cambridge Dictionary of American English, for the word "recess," Cambridge University Press, 3 pages (2000).
Certified Preliminary Amendment for U.S. Pat. No. 10,827,954, issued on Nov. 10, 2020.
Certified Preliminary Amendment for U.S. Pat. No. 10,973,443, issued on Apr. 13, 2021.
CGMS Changing Diabetes Management: Kevin Sayer, DIC Interview Transcript, 11 pages (2019).
Deciding When to Submit a 510(k) for a Change to an Existing Device, Guidance for Industry and Food and Drug Administration Staff, U.S. Department of Health and Human Services, Food and Drug Administration, 78 pages (2017).
Deciding When to Submit a 510(k) for a Software Change to an Existing Device, Guidance for Industry and Food and Drug Administration Staff, U.S. Department of Health and Human Services, Food and Drug Administration, 32 pages (2017).
Dexcom (DXCM) / Feb. 27, 2018 / 2017 Q4 Earnings call transcript, 12 pages (2017).
DexCom (DXCM) Q1 2018 Results—Earnings Call Transcript, 4 pages (2018).
Dexcom CEO—Prime Position in Our Market—Mad Money—CNBC.mp4, 4 pages (2023).
Dexcom G6, Continuous Glucose Monitoring System, User Guide, 22 pages (2020).
Dexcom G6, Continuous Glucose Monitoring System, User Guide, 7 pages (2020).
Dexcom G6, Start Here Set Up, Dexcom G6 Continuous Glucose Monitoring (CGM) System (G6), 8 pages (2019).
Dexcom G6, Using Your G6, 7 pages (2020).
DexCom, Inc. NasdaqGS:DXCM, Company Conference Presentation, 10 pages (2020).
DexCom, Inc. NasdaqGS:DXCM, Company Conference Presentation, 11 pages (2019).
DexCom, Inc. NasdaqGS:DXCM, Company Conference Presentation, 17 pages (2021).
Email from Sophie Hood to Matthew Werdegar and Manuela Cabal re. *Abbott Diabetes Care, Inc et al. v. DexCom, Inc.* | Case No. 21-977-KAJ, dated Jan. 24, 2023.
FDA News Release, FDA authorizes first fully interoperable continuous glucose monitoring system, streamlines review pathway for similar devices, 3 pages (2018).
Figures 13 and 12 of U.S. Pat. No. 10,973,443 B2 issued on Apr. 13, 2021.
Hoss, et al., Continuous Glucose Monitoring in Subcutaneous Tissue Using Factory-Calibrated Sensors: A Pilot Study, Diabetes Technology & Therapeutics, vol. 12, No. 8, pp. 591-597 (2010).
Hoss, et al., Continuous glucose monitoring in the tissue: Do we really need to calibrate in-Vivo?, Abbott Diabetes Care, 23 pages (2009).
Hoss, et al., Feasibility of Factory Calibration for Subcutaneous Glucose Sensors in Subjects with Diabetes, Journal of Diabetes Science and Technology, vol. 8(1), pp. 89-94 (2014).
IEEE 100, The Authoritative Dictionary, Seventh Edition, Standards Information Network, IEEE Press, 3 pages (2000).
Interview with Dexcom CEO, Dexcom CEO Kevin Sayer Explains G6, Written by: Michelle Boise, 10 pages—Exhibit 113 (2018).
Interview with Dexcom CEO, Dexcom CEO Kevin Sayer Explains G6, Written by: Michelle Boise, 10 pages—Exhibit 158 (2018).
Interview with Dexcom CEO, Dexcom CEO Kevin Sayer Explains G6, Written by: Michelle Boise, 9 pages (2018).
Joint Declaration under 37 C.F.R. § 1.131 for U.S. Appl. No. 15/963,828 (2020).
Letter from Department of Health & Human Services to Abbott Diabetes Care, Inc. re. PMA approval for P050020, FreeStyle Navigator Continuous Glucose Monitoring System, dated Mar. 12, 2008.
Merriam-Webster's Collegiate Dictionary, Tenth Edition for the words "housing" and "recess," Merriam-Webster, Incorporated, 4 pages (1999).

(56) References Cited

OTHER PUBLICATIONS

Merriam-Webster's Collegiate Dictionary, Tenth Edition for the words "release" and "retain," Merriam-Webster, Incorporated, 4 pages (1999).

Non-Final Office Action for U.S. Appl. No. 14/884,622, mailed on Jun. 13, 2018.

Non-Final Office Action for U.S. Appl. No. 17/030,030, issued on Dec. 17, 2020.

Notice of Allowance for U.S. Appl. No. 15/963,828, mailed on Mar. 3, 2021.

Omnipod image, Exhibit 182, 2 pages (Sep. 22, 2022).

Program Book, 2$^{nd}$ International Conference on Advanced Technologies & Treatments for Diabetes, Athens, Greece, 4 pages (2009).

Response to Non-Final Office Action under 37 C.F.R. 1.111 for U.S. Appl. No. 15/963,828, filed Dec. 8, 2020.

Response to Restriction Requirement for U.S. Appl. No. 14/884,622, filed Apr. 5, 2018.

Spruce Point Capital Management, Dexcom, Inc., Investment Research Report, Does Dexcom Really Have A Future If It Can't Match Abbott's Scale? 2 pages (Mar. 21, 2019).

Tegnestedt, et al., Levels and sources of sound in the intensive care unit—an observational study of three room types, Acta Anaesthesiol Scandinavica Foundation, 11 pages (2013).

The Chambers Dictionary for the word "retract," Chambers Harrap Publishers Ltd, 4 pages (1998).

The MiniMed Paradigm® Real-Time Insulin Pump and Continuous Glucose Monitoring System, Insulin Pump User Guide, Medtronic, Paradigm® 522 and 722 Insulin Pumps User Guide, 25 pages (2008).

The New Oxford American Dictionary, for the word "retract," Oxford University Press, 3 pages (2001).

The New Penguin English Dictionary, for the word "recess," Penguin Books, 4 pages (2000).

Watkin, An Introduction to Flash Glucose Monitoring, 16 pages (2013).

Webster's II New College Dictionary, for the word "alcove," 2 pages (2001).

Webster's Third New International Dictionary of the English Language Unabridged, for the word "retract," Merriam-Webster Inc., 5 pages (1993).

Hoss, U. et al., "Factory-Calibrated Continuous Glucose Sensors: The Science Behind the Technology", Diabetes Technology & Therapeutics, vol. 19, Suppl. 2, pp. S-44-S-50 (2017).

Dock, E. et al., "Multivariate data analysis of dynamic amperometric biosensor responses from binary analyte mixtures—application of sensitivity correction algorithms", Talanta, 65, pp. 298-305 (2005).

Hanson, K. et al., "Comparison of Point Accuracy Between Two Widely Used Continuous Glucose Monitoring Systems", Journal of Diabetes Science and Technology, 2024, pp. 1-10.

Abbott Press Release—"Abbott Receives CE Mark for FreeStyle® Libre, A Revolutionary Glucose Monitoring System for People with Diabetes" retrieved from https://abbott.mediaroom.com/2014-09-03-Abbott-Receives-CE-Mark-for-FreeStyle-Libre-a-Revolutionary-Glucose-Monitoring-System-for-People-with-Diabetes/, Sep. 3, 2014, 3 pages.

Abbott Press Release—"Abbott Receives FDA Approval for the FreeStyle Libre Pro™ System, A Revolutionary Diabetes Sensing Technology for Healthcare Professionals to Use with their Patients" retrieved from https://abbott.mediaroom.com/2016-09-28-Abbott-Receives-FDA-Approval-for-the-FreeStyle-Libre-Pro-System-a-Revolutionary-Diabetes-Sensing-Technology-for-Healthcare-Professionals-to-use-with-their-Patients/, Sep. 28, 2016, 5 pages.

Abbott Press Release—"Abbott's FreeStyle® Libre 14 Day Flash Glucose Monitoring System Now Approved in U.S." retrieved from https://abbott.mediaroom.com/2018-07-27-Abbotts-FreeStyle-R-Libre-14-Day-Flash-Glucose-Monitoring-System-Now-Approved-in-U-S/, Jul. 27, 2018, 3 pages.

Alcock, et al., "Continuous Analyte Monitoring to Aid Clinical Practice", IEEE Engineering in Medicine and Biology, vol. 13, No. 3, pp. 319-325 (1994).

ANZHSN, National Horizon Scanning Unit Horizon Scanning Report, "GlucoWatch® G2 Biographer for the non-invasive monitoring of glucose levels", 46 pages, May 2004.

Cather, CGM Frustrations Survey dated Jun. 2020, 37 pages in *Abbott Diabetes Care Inc., et al. v. Dexcom, Inc.*, Case No. 1:21-cv-00977-KAJ (District of Delaware).

Chen, et al., "In vivo Glucose Monitoring with Miniature "Wired" Glucose Oxidase Electrodes", Analytical Sciences, vol. 17 Supplement, pp. i297-i300 (2001).

Clinical Trials, Competitor and Ecosystem Players dated Jun. 25, 2020, 29 pages in *Abbott Diabetes Care Inc., et al. v. Dexcom, Inc.*, Case No. 1:21-cv-00977-KAJ (District of Delaware).

Declaration of Dr. Anthony Edward Cass in Support of Petition for Inter Partes Review of U.S. Pat. No. 11,020,031 in *Abbott Diabetes Care Inc. v. Dexcom, Inc.*, Case No. IPR2024-00890, In the United States Patent and Trademark Office, Before the Patent Trial and Appeal Board, May 10, 2024, 138 pages.

Declaratiom of Karl R. Leinsing, MSME, PE, in Support of Abbott's Motion for Summary Judgment dated May 19, 2023, 81 pages in *Abbott Diabetes Care Inc., et al. v. Dexcom Inc.*, Case No. 1:21-CV-00977-KAJ (District of Delaware).

Dock, et al., "Multivariate data analysis of dynamic amperometric biosensor responses from binary analyte mixtures—application of sensitivity correction algorithms", Talanta, 65:298-305 (2005).

Effectiveness and Safety Study of the DexCom™ G4 Continuous Glucose Monitoring System, DexCom, Inc, U.S. National Library of Medicine, ClinicalTrials.gov Identifier: NCT01111370, 4 pages (2017).

E-mail Communication from Christopher M. Dougherty regarding Bi Monthly Global Commercial Insights Meeting dated Dec. 17, 2019, 69 pages in *Abbott Diabetes Care Inc., et al. v. Dexcom, Inc.*, Case No. 1:21-cv-00977-KAJ (District of Delaware).

Feldman, et al., "A Continuous Glucose Sensor Based on Wired Enzyme™ Technology—Results from a 3-Day Trial in Patients with Type 1 Diabetes", Diabetes Technology & Therapeutics, vol. 5, No. 5, pp. 769-779 (2003).

Design U.S. Appl. No. 29/101,218, filed Feb. 25, 1999, 11 pages.

U.S. Pat. No. 11,020,031 issued Jun. 1, 2021, 1058 pages.

Fraser, "An Introduction to in vivo Biosensing: Progress and Problems", Biosensors in the Body: Continuous In Vivo Monitoring, pp. 1-56 (1997).

FreeStyle Libre 2 HCP Pulse, Mar. 2021 Report, dated Mar. 1, 2021, 14 pages in *Abbott Diabetes Care Inc., et al. v. Dexcom, Inc.*, Case No. 1:21-CV-00977-KAJ (District of Delaware).

FreeStyle Navigator Continuous Glucose Monitoring System, User's Guide, Abbott Diabetes Care Inc., 38 pages (2008).

Frost, et al., "Implantable chemical sensors for real-time clinical monitoring: progress and challenges", Current Opinion in Chemical Biology, 6:633-641 (2002).

Godek, et al., Chapter 2, "The Macrophage in Wound Healing Surrounding Implanted Devices", In Vivo Glucose Sensing, 36 pages (2010).

Gross, et al., "Performance Evaluation of the MiniMed® Continuous Glucose Monitoring System During Patient Home Use", Diabetes Technology & Therapeutics, vol. 2, No. 1, pp. 49-56 (2000).

Heller, "Implanted Electrochemical Glucose Sensors for the Management of Diabetes", Annu. Rev. Biomed. Eng., 01:153-175 (1999).

Heller, "Integrated Medical Feedback Systems for Drug Delivery", American Institute of Chemical Engineers Journal, vol. 51, No. 4, pp. 1054-1066 (2005).

Heller, et al., "Electrochemical Glucose Sensors and Their Applications in Diabetes Management", Chem. Rev., 108, Parts 1-3, pp. 2482-2505 (2008).

Henning, Chapter 5, "Commercially Available Continuous Glucose Monitoring Systems", In Vivo Glucose Sensing, 50 pages (2010).

Koudelka-Hep, "Electrochemical Sensors for in vivo Glucose Sensing", Biosensors in the Body: Continuous In Vivo Monitoring, 12 pages (1997).

(56) References Cited

OTHER PUBLICATIONS

Kovatchev, et al., "Evaluating the Accuracy of Continuous Glucose-Monitoring Sensors", Diabetes Care, vol. 27, No. 8, pp. 1922-1928 (2004).

Lesperance, et al., "Calibration of the Continuous Glucose Monitoring System for Transient Glucose Monitoring", Diabetes Technology & Therapeutics, vol. 9, No. 2, pp. 183-190 (2007).

Nishida, et al., "Development of a ferrocene-mediated needle-type glucose sensor covered with newly designed biocompatible membrane, 2-methacryloyloxyethyl phosphorylcholine-co-n-butyl methacrylate", Medical Progress through Technology, 21:91-103 (1995).

Project Status Update, Glucose Sensor Applicator Dexcom (project #2554), Design Concepts, Inc., 6 pages (2014).

Schlosser, et al., "Biocompatibility of Active Implantable Devices", Biosensors in the Body: Continuous in vivo Monitoring, 34 pages (1997).

Schmidt, et al., "Calibration of a wearable glucose sensor", The International Journal of Artificial Organs, vol. 15, No. 1, pp. 55-61 (1992).

Seagrove Partners, International Diabetes Device, 2022 Blue Book dated 2022, 143 pages in *Abbott Diabetes Care Inc., et al.* v. *Dexcom, Inc.*, Case No. 1:21-cv-00977-KAJ (District of Delaware).

Velho, et al., "Strategies for calibrating a subcutaneous glucose sensor", Biomed. Biochim. Acta 48:11/12, pp. 957-964 (1989).

Wilson et al., Chapter 1, "Introduction to the Glucose Sensing Problem," In Vivo Glucose Sensing, 32 pages (2010).

Wisniewski, et al., "Characterization of implantable biosensor membrane biofouling", Fresenius J Anal Chem, 366:611-621 (2000).

Dorland's Illustrated Medical $31^{st}$ Edition Dictionary, definition of "fluid, intersitial", (2007), 3 pages.

Forlenza, G.P., et al., "Factory-Calibrated Continuous Glucose Monitoring: How and Why It Works, and the Dangers of Reuse Beyond Approved Duration of Wear", Diabetes Technology & Therapeutics, vol. 21, No. 4, (2019) 13 pages.

Stephens Inc., Research Bulletin, "DexCom, Inc., A True Game Changer: The G6 Eliminates Fingersticks", (2018) 5 pages.

The American Hertiage® Medical Dictionary, definition of "cathether" and "interstitial fluid", (2007), 4 pages.

\* cited by examiner

SENSITIVITY CALIBRATION OF IN VIVO SENSORS USED TO MEASURE ANALYTE CONCENTRATION

RELATED APPLICATIONS

The present application is a continuation of U.S. patent application Ser. No. 16/256,855 filed Jan. 24, 2019, which is a continuation of U.S. patent application Ser. No. 15/789,949 filed Oct. 20, 2017, now U.S. Pat. No. 10,188,334, which is a continuation of U.S. patent application Ser. No. 15/616,916 filed Jun. 7, 2017, now U.S. Pat. No. 9,801,577, which is a continuation of U.S. patent application Ser. No. 14/066,650 filed Oct. 29, 2013, now U.S. Pat. No. 9,675,290, which claims priority to U.S. Provisional Application No. 61/720,393 filed Oct. 30, 2012, entitled "Sensitivity Calibration of In Vivo Sensors Used to Measure Analyte Concentration", the disclosure of which is incorporated herein by reference for all purposes.

BACKGROUND

The detection of the concentration level of glucose or other analytes in certain individuals may be vitally important to their health. For example, the monitoring of glucose levels is particularly important to individuals with diabetes or pre-diabetes. People with diabetes may need to monitor their glucose levels to determine when medication (e.g., insulin) is needed to reduce their glucose levels or when additional glucose is needed.

Devices have been developed for automated in vivo monitoring of analyte concentrations, such as glucose levels, in bodily fluids such as in the blood stream or in interstitial fluid. Some of these analyte level measuring devices are configured so that at least a portion of the devices are positioned below a skin surface of a user, e.g., in a blood vessel or in the subcutaneous tissue of a user. As used herein, the term analyte monitoring system is used to refer to any type of in vivo monitoring system that uses a sensor disposed with at least a portion subcutaneously to measure and store sensor data representative of analyte concentration levels automatically over time. Analyte monitoring systems include both (1) systems such as continuous glucose monitors (CGMs) which transmit sensor data continuously or at regular time intervals (e.g., once per minute) to a processor/display unit and (2) systems that transfer stored sensor data in one or more batches in response to a request from a processor/display unit (e.g., based on an activation action and/or proximity, for example, using a near field communications protocol) or at a predetermined but irregular time interval.

Determining an analyte concentration level in blood based on the analyte concentration measured using an analyte monitoring system typically involves calibrating the in vivo sensor of the analyte monitoring system using a reference measurement. For example, a finger stick blood sample may be used as a reference to determine the blood analyte concentration at a particular time and the result is paired with a corresponding measurement from the analyte monitoring system. The sensitivity of the analyte monitoring system's sensor is adjusted based on the difference and other factors. However, several factors related to the measurement from the analyte monitoring system can affect the accuracy of the calibration. Thus, what is needed are systems, methods and apparatus to improve sensitivity calibration of the in vivo sensors used to measure analyte concentration.

SUMMARY

Methods, devices, and systems are provided to improve sensitivity calibration of an in vivo analyte sensor and usability of the associated analyte monitoring system. In some embodiments, the present disclosure includes a computer-implemented method for defining a set of system checks associated with an analyte monitoring system; receiving a request to perform calibration of an in vivo sensor of an analyte monitoring system; receiving a signal representative of sensor data from the analyte monitoring system related to an analyte level of a patient measured over time; conducting calibration using a reference measurement estimated at calibration time from a first predetermined duration of reference observation paired, with a signal representative of sensor data up to the calibration time; updating calibration using the same reference measurement at a second predetermined duration of reference observation spanning the first predetermined duration and an additional period, paired with a signal representative of sensor data up to a third predetermined period relative to the calibration time; using an adjustment map that balances the risk of over and under calibration based on a priori information; deferring calibration if attenuation of a signal from the sensor is detectable at a time in which the request is received, wherein the calibration is delayed until the signal attenuation is no longer detected; performing calibration if the set of system checks pass and signal attenuation is not being detected; storing the signal from the sensor over time for a period of time spanning from before the calibration to after the calibration; determining if previously undetected signal attenuation occurred during the calibration based on the stored signal after the calibration has completed; reconstructing the signal and revising the calibration of the sensor based on the reconstructed signal if previously undetected signal attenuation occurred and if the signal can be adjusted to compensate for the previously undetected signal attenuation; invalidating the calibration and requesting a new calibration if previously undetected signal attenuation occurred and if the signal cannot be adjusted to compensate for the previously undetected signal attenuation; and displaying an analyte concentration value if previously undetected signal attenuation did not occur during calibration based on the stored signal. Related systems and computer program products are also disclosed. Numerous other aspects and embodiments are provided. Other features and aspects of the present disclosure will become more fully apparent from the following detailed description, the appended claims, and the accompanying drawings.

DETAILED DESCRIPTION

Figure 1:
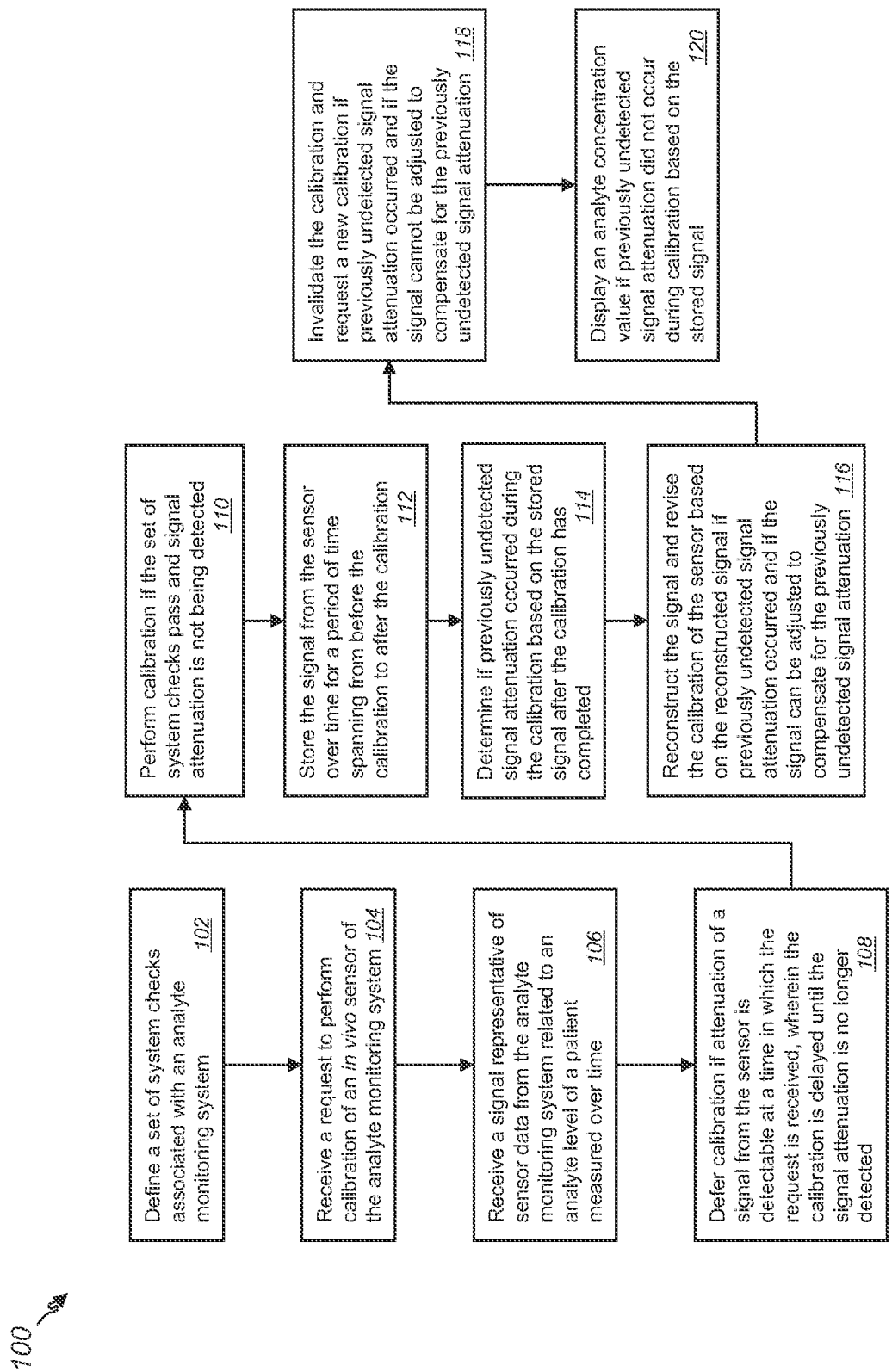
FIG. 1 depicts a flowchart illustrating an example of a first method for calibrating a sensor of an analyte monitoring system in accordance with some embodiments of the present disclosure.

The present disclosure provides systems, methods, and apparatus to improve sensitivity calibration of an in vivo analyte sensor and usability of the associated analyte monitoring system. In some embodiments, the present disclosure provides methods that improve the user experience of using an analyte monitoring system. For example, in some embodiments, the present disclosure includes features that reduce the amount of calibration or re-calibration performed by the analyte monitoring system. More specifically, in some embodiments, the present disclosure provides methods of using a suspect calibration attempt to avoid having to recalibrate by adjusting the calibration or mitigating effects of sensor signal attenuation that caused the calibration attempt to be suspect. For example, sensor signal attenuating phenomena such as Early Sensitivity Attenuation (ESA) and dropouts that occur during a calibration attempt (and render the calibration attempt suspect) can be addressed in some embodiments. When ESA or a dropout occurs, the sensor still generates a signal with a lower amplitude than the true signal, but may still take on a value that is physiologically feasible. Hence, unlike signal loss, detection of either ESA or a dropout is not trivial. Unlike typical noise artifact, ESA and dropouts consistently bias the sensor output down. Standard filtering methods are not effective to compensate for neither ESA nor dropouts without incurring additional drawbacks. ESA typically occurs within the first few hours of sensor start time, and disappears thereafter. Dropouts last for much shorter periods and might occur, for example, during bedtime independent of the sensor start time.

In some embodiments, the present disclosure provides methods of analyzing sensor data received after a reference analyte concentration value is received (e.g., initiated by the user) to perform a calibration in place of a future system requested calibration. Thus, for example, if a user happens to perform a finger stick in vitro blood glucose (BG) measurement and the outcome is provided to the analyte monitoring system, the system can use the information as a reference analyte concentration value for a calibration attempt. In conventional BG systems, a reference analyte BG reading is computed based on a time series measurement in response to an analyte sample collected in a test strip. The BG system takes a predetermined duration in order to collect the time series measurement, typically in the five second range. In addition, instead of determining a sensitivity of the in vivo sensor using a real time algorithm that only considers limited sensor data in order to provide real time responsiveness regarding the success or failure of the calibration attempt, the present disclosure can take the time to consider a wider window of sensor data since the user is not waiting for an outcome indication of the calibration attempt. Therefore, not only are the number of system requested calibrations reduced, more accurate calibrations can be performed by using more data. In some embodiments, the present disclosure provides methods that improve the sensitivity calibration by using historical data to hedge against the aggregate risks of calibration errors, such as, for example, due to ESA. In some embodiments, the present disclosure uses "extra" data obtained from a test strip that remains in a BG meter after an initial reading has been made, to improve the accuracy of the initial reading and to improve the certainty of the analyte monitoring system's calibration based on the initial reading. In some embodiments, the present disclosure uses fault identification, instead of merely detecting faults, to improve the likelihood of a successful calibration attempt.

Embodiments of the present disclosure are described primarily with respect to continuous glucose monitoring devices and systems for illustrative purposes but the present disclosure can be applied to other analytes, other analyte characteristics, and other analyte measurement systems, as well as data from measurement systems that transmit sensor data from a sensor unit to another unit such as a processing or display unit in response a request from the other unit. For example, other analytes that can be monitored include, but are not limited to, acetyl choline, amylase, bilirubin, cholesterol, chorionic gonadotropin, creatine kinase (e.g., CK-MB), creatine, DNA, fructosamine, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, can also be monitored. In those embodiments that monitor more than one analyte, the analytes can be monitored at the same or different times. In addition, in some embodiments, the present disclosure can be applied to non-analyte sensor data. For example, non-analyte sensor data can include temperature estimation of a target physiological compartment that is made based on measuring the temperature of a nearby compartment, where the measured temperature is related to the temperature of the target compartment. The present disclosure also provides numerous additional embodiments.

Some embodiments of the present disclosure include a programmed computer system adapted to receive and store data from an analyte monitoring system. The computer system can include one or more processors for executing instructions or programs that implement the methods described herein. The computer system can include memory and persistent storage devices to store and manipulate the instructions and sensor data received from the analyte monitoring system. The computer system can also include communications facilities (e.g., wireless and/or wired) to enable transfer of the sensor data from the analyte monitoring system to the computer. The computer system can include a display and/or output devices for identifying dropouts in the sensor data to a user. The computer system can include input devices and various other components (e.g., power supply, operating system, clock, etc.) that are typically found in a conventional computer system. In some embodiments, the computer system is integral to the analyte monitoring system. For example, the computer system can be embodied as a handheld or portable receiver unit within the analyte monitoring system. In some embodiments, the analyte monitoring system may include a computer system and in some embodiments, the analyte monitoring system may include (or be in signal communication with) an analyte meter (e.g., a BG meter) configured to measure an analyte concentration in vitro.

In some embodiments, the various methods described herein for performing one or more processes, also described herein, can be embodied as computer programs (e.g., computer executable instructions and data structures). These programs can be developed using an object oriented programming language, for example, that allows the modeling of complex systems with modular objects to create abstractions that are representative of real world, physical objects and their interrelationships. However, any practicable programming language and/or techniques can be used. The software for performing the inventive processes, which can be stored in a memory or storage device of the computer system described herein, can be developed by a person of ordinary skill in the art based upon the present disclosure and can include one or more computer program products. The computer program products can be stored on a non-transitory computer readable medium such as a server memory, a computer network, the Internet, and/or a computer storage device.

Analyte monitoring systems such as Continuous Glucose Monitor (CGM) systems that use reference Blood Glucose (BG) values for calibration, pair the reference BG values with a corresponding sensor data point received in an uncalibrated sensor signal from the CGM system. There are a number of conditions which can invalidate a calibration attempt due to known hardware system, environmental, and physiological factors. A hardware system invalidating factor example includes the sensor signal transmission to the receiver, handheld, or monitoring unit has been compromised with noise or interrupted altogether. A potential environmental invalidating factor example occurs when a measured temperature is out of the operating range of the system. A physiological invalidating example occurs when the computed rate is too high, either physiologically so, such that the accuracy of certain numerical calculations can be suspect, or non-physiologically high such that the reliability of the latest sensor signal is questionable.

Temporal features of the sensor signal that do not correlate to glucose excursion can significantly affect calibration. Examples of such temporal features include Early Sensitivity Attenuation (ESA) and dropouts. Methods to detect and evaluate these features during operation of the analyte monitoring system as they occur (i.e., in real time) allows the system to determine the proper course of action. For example, if a dropout is determined to be taking place while the system is scheduled to perform a calibration, the system can delay the calibration request until the undesired artifact is deemed to have ended. On occasion, re-evaluating data from before and up to after a completed calibration can reveal that the completed calibration actually took place while an undesired temporal feature, such as a dropout, occurred. This retrospective conclusion can result in two possible scenarios. The first is that the errors in calibration due to the dropout can be corrected, so that the system revises the calibration in light of this new information. The second is that the errors in calibration due to the dropout cannot be corrected. In this case, the system may decide to invalidate the recently performed calibration either immediately or within a certain elapsed time after this determination. When the recently performed calibration is invalidated, the system will determine when to request a new calibration based on various factors including the likelihood of the persistence of undesired temporal features.

In some embodiments, the present disclosure attempts to adjust the calibration and/or mitigate the effect of temporal signal attenuations on calibration. By combining existing calibration checks and calculations with retrospective calibration and both real-time and retrospective artifact detection, such as for example, using a dropout detector, the present disclosure is able to salvage suspect calibration attempts that might otherwise require additional calibration.

Turning now to FIG. 1, an example of a method 100 according to the present disclosure is illustrated in a flowchart. As mentioned above, an analyte monitoring system can include a set of system tests or checks to determine if a calculated sensitivity value is acceptable and can be used to configure a sensor (102). For example, the system checks may include an outlier check, a comparison against sensor-code nominal sensitivity in the calibration validations check, a stability check, a calibration sensitivity check, an ESA check, and the like. When the system determines that calibration of the sensor should be performed, the system can request that the user provide a reference analyte concentration value (104). Sensor data continues to be received from the in vivo sensor while the request is pending (106). Known methods and apparatus for detecting undesired signal attenuation are used to determine if calibration should be deferred dues to signal attenuation (108). For example, U.S. Pat. No. 7,630,748 entitled "Method and System For Providing Analyte Monitoring" and incorporated herein by reference, describes a real-time dropout detector that may be used.

If undesired signal attenuation is detected, the system will delay the calibration request until the sensor has recovered and a true signal is generated. Otherwise, the system will allow calibration provided that other system checks are passed (110). The system stores the sensor data from before and after the calibration (112). Within a predetermined time after a calibration has been performed, the system retrospectively evaluates the sensor's signal quality around the moment of calibration to determine whether a previously undetected undesired signal attenuation was missed by the real-time detector(s) (114). If an undesired signal attenuation is determined to have taken place during the calibration, and if the true analyte signal can be reconstructed with good confidence, then the system revises the result of the calibration without the need of further user interaction (116). An example of such retrospective calibration is described in U.S. Pat. No. 7,618,369 entitled "Method and System For Dynamically updating Calibration Parameters For an Analyte Sensor" and incorporated herein by reference. However, if an undesired signal attenuation is determined to have taken place and the true analyte signal cannot be reconstructed with good confidence, then the system may request a new calibration (118).

In some embodiments, the system can take alternative courses of action depending on the characterization of the attenuation. In order to characterize attenuation, a detector estimates the degree of attenuation during a window of time by comparing the measured aggregate level of the signal in that window relative to a baseline level, which is computed from the same window of time using a different filter, or computed from a different window of time using a similarly structured filter. The comparison between the measured aggregate level and the baseline level is used to identify whether or not an attenuation is occurring. If adjacent time windows are deemed to be attenuated, then the time windows may be considered as a single attenuation event. For each event, a predicted time of onset and recovery may be computed. Some of the characterizations of attenuation include the direct ratio between the measured aggregate level and its baseline, a scaled ratio between the measured aggregate level and its baseline, a function such as a quadratic absolute ratio between the measured aggregate level and its baseline, the peak ratio, the duration between onset and recovery, or the area under the curve generated by the ratio and duration. One or more of these characterizations can be used to determine the various courses of action needed. If the attenuation completely invalidates the previously completed calibration, then the system can immediately expire that calibration, and the system may no longer display an analyte concentration value until a successful calibration has been performed. If the calibration is sufficiently accurate enough to provide useful analyte concentration value information for at least a short time after the calibration, the system momentarily allows the analyte concentration value display to continue, and then expires the calibration soon after. When appropriate, the system requests a new calibration in order to resume display of the analyte concentration value (120).

In some embodiments, in addition to compensating for signal attenuation, the methods of the present disclosure can assess the feasibility of a calibration attempt based on past and stored data to identify faults. Thus, instead of merely invalidating a calibration attempt because a check has failed, the present disclosure can determine useful information to avoid repeating failed calibrations in the future. The present disclosure assesses the sensor signal and reference analyte value history around the present and past calibration attempts. In some embodiments, the present disclosure determines whether a current failed calibration attempt is caused by the sensor currently producing unreliable sensor data, or whether the reference analyte concentration value is not reliable.

To illustrate the additional information provided by checking the reference value and the sensor data instead of just the sensitivity value, consider a case in which the latest calibration attempt is close enough to a prior attempt, whether or not the prior attempt was used to update sensitivity for glucose calculation. In addition to the system checks, these relatively closely spaced reference values can be compared to assess the feasibility of the reference value of the latest calibration attempt. For example, if the difference between the latest and previous reference values is too large considering the time interval between them and the assumed reference value measurement error variability, then the latest calibration attempt should be failed, even though none of the sensitivity based checks failed. In some cases, an outlier reference value could occur such that the sensitivity happens to be relatively unchanged because the error in reference value is almost cancelled by another erroneous factor in the calculation of sensitivity.

If there are several recent past reference value data available, other methods can be used. One example is to monitor the standard deviation of the predicted reference value using a regularization procedure or other data smoothing procedure. A dramatic increase in standard deviation around the latest attempt implies that the latest reference value has a relatively large uncertainty.

In addition to using reference value, one can make a better assessment of the latest calibration attempt by considering the sensor data. For example, given the best sensitivity used up to the latest attempt, the computed analyte level can be compared from the sensor data around the instances where recent past calibration attempts were made. The computed analyte level can then be tested against similar methods as described in the previous section. In addition, methods that require relatively constant sample time, such as an Auto Regressive (AR) model and Auto Regressive Moving Average (ARMA), can be used to see whether the latest sensor measurements correlated reasonably well to past data in the same manner as observed around the recent past attempts. Because of the relatively rich data content from the sensor, assessments can be made involving combinations of point wise analyte values as well as higher order signals. For example, one can track the analyte rate of change during recent past and latest calibration attempts, to determine whether including the latest calibration attempt significantly changes the rate distribution statistics of the moving average population.

The likelihood of undesired sensor transients can be checked to see if they differ dramatically between the latest attempts. For example, assuming a dropout detector is used to assess the likelihood of the sensor signal exhibiting dropouts, if the detector generates a much higher likelihood for dropouts than the previous attempts, then it is possible that at least the absolute raw sensor signal and/or the raw sensor rate of change may be far enough from the true value that a sensitivity check may not indicate an actual change in sensitivity. The combined knowledge of the relative confidence of the sensor, reference BG, and the resulting sensitivity calculation amongst relatively recent attempts can be useful in a number of ways. For example, the reference value and sensor signal comparisons are useful in qualifying the relative uncertainty of calibration attempts. By taking the combined information, one can weigh both the reference BG and sensor signal of recent past attempts, so that future calibration attempts can be compared against these values without having to resort to using equal weighting for each of the attempts. This results in a more reliable relative assessment. In some embodiments, the relative weighting can be used when generating the latest weighted sensitivity to be used in converting raw sensor signal into final glucose values as well as glucose rate of change. In other words, instead of using a fixed weighting factor that was predetermined offline, each calibration update can use all near past and latest attempts with weights that are derived from the combination of the above comparisons.

Additionally, a consistent pattern of increase or change in uncertainty over time of the sensor signal, reference value, or computed sensitivity can be used to infer that state of the system. Several possible scenarios and corresponding system actions are described below. For example, if the latest few attempts indicate that the sensor signal or sensor rate of change uncertainty increases dramatically compared to the older attempts, the system could conclude that the sensor is momentarily not ready to produce reliable measurements. The system could notify the user to delay the follow-up calibration attempt in order not to waste their effort. The delay time may depend on other checks, such as the various components of data quality check as well as the ESA detector. If the last attempt indicates that the latest reference value uncertainty is dramatically larger compared to the other past attempts, the system could conclude that the attempt must be failed because the latest reference value is likely to be an outlier. The system could notify the user to try again, possibly reminding the user to consult the user guide for the proper finger stick method.

If more than one recent reference value attempts show a relatively larger uncertainty than the older records, then the system can conclude that something systematic could be wrong with the reference value measurement process. Examples include using a new test strip vial but not correctly updating the sensor code, using alternate site testing (AST) without properly preparing the test area, and possibly using control solution instead of patient's blood as a sample source. The system could remind the user to consult the user guide for the proper finger stick method. If the persistent increase in uncertainty is too big, the system may decide to terminate operation to prevent producing results with poor accuracy.

If more than one attempt indicate that while both the reference value and the sensor signal are relatively reasonable, but the latest computed sensitivities result in a much larger uncertainty than before, then it is possible that a dramatic change has occurred. One possible cause would be a change in the effective dynamics between, for example, blood and interstitial glucose, such that the reference value and interstitial analyte value independently show no dramatic change in behavior, but their dynamic and possibly static relationship has changed. Another possible cause would be the loss of counter electrode function, in which a bias is introduced between measured interstitial analyte and blood analyte as measured by the reference value. In some embodiments, the system could elect to adjust the calibration factor with an offset factor as necessary. If several follow-up confirmatory finger sticks do not indicate that the offset-adjusted model has a good fit, then the system may decide to terminate operation.

Figure 2:
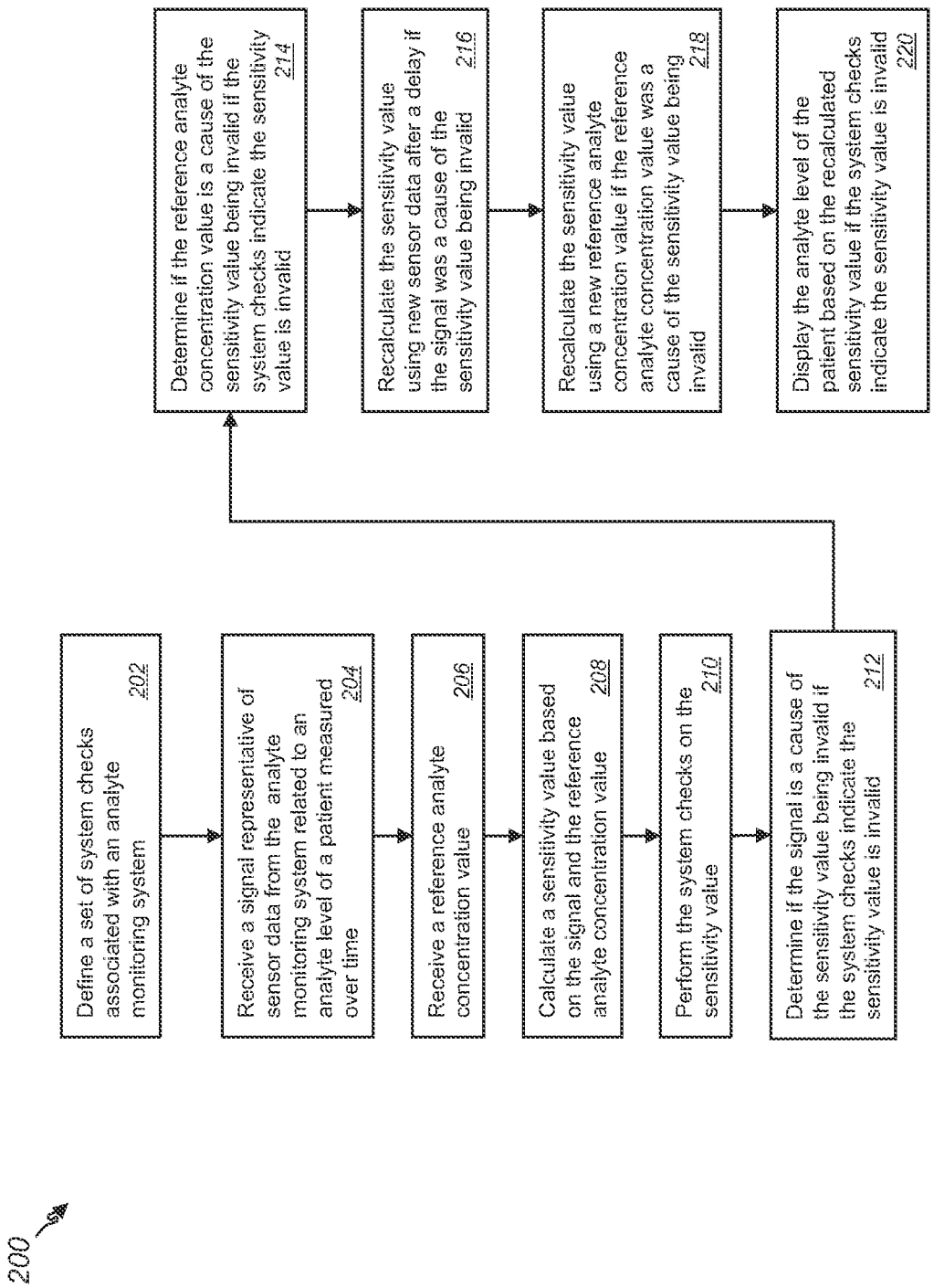
FIG. 2 depicts a flowchart illustrating an example of a second method for calibrating a sensor of an analyte monitoring system in accordance with some embodiments of the present disclosure.

FIG. 2 is a flow chart depicting an example method 200 of assessing the sensor signal and reference analyte value history around the present and past calibration attempts to determine whether a current failed calibration attempt is caused by the sensor producing unreliable sensor data, or whether the reference analyte concentration value is not reliable. Initially, a set of system checks associated with an analyte monitoring system is defined (202). A signal representative of sensor data is received from an analyte monitoring system related to an analyte level of a patient measured over time (204). A reference analyte concentration value is received (206). A sensitivity value is calculated based on the signal and the reference analyte concentration value (208). The system checks are performed on the sensitivity value (210). If the system checks indicate the sensitivity value is invalid, the system determines if the signal is a cause of the sensitivity value being invalid (212). If the system checks indicate the sensitivity value is invalid, the system determines if the reference analyte concentration value is a cause of the sensitivity value being invalid (214). The sensitivity value is recalculated using new sensor data after a delay if the signal was a cause of the sensitivity value being invalid (216). The sensitivity value is recalculated using a new reference analyte concentration value if the reference analyte concentration value was a cause of the sensitivity value being invalid (218). The analyte level of the patient is displayed based on the recalculated sensitivity value if the system checks indicate the sensitivity value is invalid (220).

Figure 3:
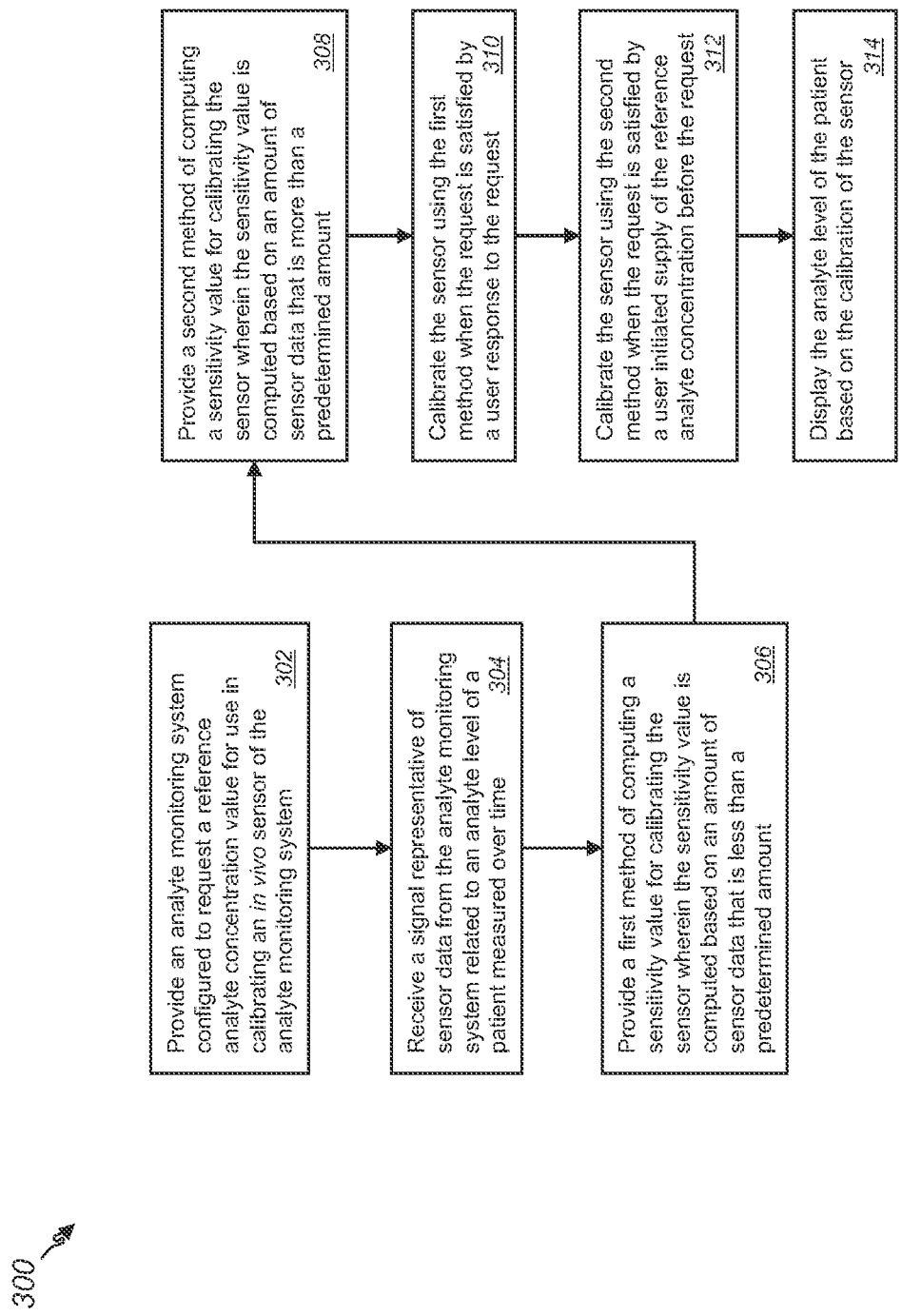
FIG. 3 depicts a flowchart illustrating an example of a third method for calibrating a sensor of an analyte monitoring system in accordance with some embodiments of the present disclosure.

Turning now to FIG. 3, another aspect of the present disclosure is described. In some embodiments, where a user-initiated provision of a reference analyte concentration value that happens to occur within a predetermined time period of a scheduled calibration request, is to be used for calibration, a retrospective review of the calibration may be used to improve the calibration. In other words, instead of determining a sensitivity of the in vivo sensor using a real-time algorithm that only considers limited sensor data in order to provide real-time responsiveness regarding the success or failure of the calibration attempt, the present disclosure can consider a wider window of sensor data since the user is not expecting feedback regarding a calibration attempt or, for that matter, the user is not aware of the calibration attempt at all.

FIG. 3 is a flowchart depicting an example method 300 of using retrospective analysis on calibration attempts that use a user-initiated provision of a reference analyte concentration value. For example, if a user happens to perform a finger stick in vitro blood glucose (BG) measurement and the outcome is provided to the analyte monitoring system within a predetermined time period of a scheduled calibration request, the system can use the information as a reference analyte concentration value for a calibration attempt and the calibration attempt can be retrospectively analyzed to refine the calibration.

In some embodiments, an analyte monitoring system is provided configured to request a reference analyte concentration value for use in calibrating an in vivo sensor of the analyte monitoring system (302). The request may be satisfied by a user-initiated supply of the reference analyte concentration value before the request or by a user response to the request. A signal representative of sensor data is received from the analyte monitoring system related to an analyte level of a patient measured over time (304). A first method of computing a sensitivity value for calibrating the sensor is provided wherein the sensitivity value is computed based on an amount of sensor data that is less than a predetermined amount (306). A second method of computing a sensitivity value for calibrating the sensor is provided wherein the sensitivity value is computed based on an amount of sensor data that is more than a predetermined amount (308). The sensor is calibrated using the first method when the request is satisfied by a user response to the request (310). The sensor is calibrated using the second method when the request is satisfied by a user initiated supply of the reference analyte concentration before the request (312). The analyte level of the patient is displayed based on the calibration of the sensor (314).

In some embodiments, the system attempts a full retrospective calibration on a first BG measurement and a partial and/or real-time calibration on a second BG measurement as soon as a scheduled calibration is required. The result can be a weighted average based on the relative uncertainty of the two results. In some embodiments, the weighting scheme can be dependent on the percentage of data points available to perform retrospective calibration. Once a weighted average of the two calibration values are obtained, then the system can use that value as the calibration value and the user will be relieved of having to take a measurement for the next scheduled calibration. If one of the values fails a calibration-related acceptance criteria, then the system ignores that value. If none of the values pass the system checks, then the normally scheduled calibration will occur.

In some embodiments, the system can wait for the second user-initiated BG measurement to have sufficient associated sensor data so that retrospective calibration can be performed on both user-initiated BG measurements without attempting a real-time calibration. If both calibrations pass the calibration-related acceptance criteria, then the weighted average will be used as the calibration value for the next scheduled calibration. If one calibration fails, then only the successful calibration is used. If both fail, then the normally scheduled calibration will occur.

In some embodiments, any user-initiated BG measurements prior to a next scheduled calibration can be used to update calibration parameters that are used to screen out unsuitable conditions. For example, pre-calibration screening routines may check the glucose rate of change based on an assumed sensitivity value and the analyte monitoring system's sensor signal close in time to a next scheduled calibration. Updating the sensitivity value using the user-initiated BG measurements can improve the reliability of such a pre-calibration screening routine, thereby reducing the frequency of unnecessary calibration requests that have a relatively elevated chance of failure. In some embodiments, any user-initiated BG measurement taken just prior to a BG measurement initiated by the system (e.g., a system requested measurement) for a next scheduled calibration, can be combined to obtain calibration results that are relatively insensitive to BG measurement errors, an analyte monitoring system sensor signal noise, and potential changes in system equilibrium since the last scheduled calibration. In some embodiments, the decision to use any one or combination of the above embodiments can be determined by a processor-based online logic system and/or by using rules derived offline from analysis of stored data. For example, the system can determine that a stepwise change in one or more system related parameters may be likely around the third to fourth day of the sensor wear.

In another aspect of the present disclosure, the system may take advantage of additional data available when a test strip is left in a reference BG meter beyond the time required by the meter's primary algorithm to determine a reference analyte concentration value. This extended time during which an analyte measurement system with an integrated reference BG meter would not normally monitor the output of the reference BG meter can be used to refine or improve the initial determination of the reference analyte concentration value by using the additional data. A second algorithm allows for an updated reference analyte concentration value and the uncertainty limits can be used by the analyte measurement system to further refine its calibration value.

In some embodiments, for each calibration instance, the primary algorithm produces a reference BG value to be used by the analyte measurement system's calibration algorithm. The reference BG value, together with the most recent sensor signal measurements, can be used to both evaluate the suitability of the current calibration attempt and to obtain the sensitivity (i.e., a scaling calibration factor), in order to produce an analyte measurement from the analyte measurement system. Immediately after, the second algorithm can use data from the existing primary algorithm plus any further signal from the BG meter's strip port until the strip is removed. The second algorithm then provides an updated reference BG value to the analyte measurement system's calibration algorithm, which uses the updated reference BG value to refine the sensitivity value. The update can occur several minutes after the test strip has been removed and requires no special action by the user.

In some embodiments a stream of recursive revisions of the reference BG meter glucose estimate is used to obtain a measure of the measurement's variability. The variability in the reference BG meter glucose value can then be translated into the variability of the computed sensitivity for calibration. This results in both upper and lower bounds of the estimated sensitivity. Knowing these bounds allow the relative precision of each calibration to be compared. In addition, any threshold checks could be done with these bounds taken into account. For example, if the latest rate check results in an estimate of 1.9±0.5 mg/(dL min), then a +2 mg/(dL min) maximum rate threshold may be too close for the latest calibration attempt to be allowed to succeed.

In some embodiments, the reference BG meter variability is first obtained by comparing the characteristics of a primary reference BG meter algorithm against the secondary reference BG meter algorithm operating at different extended time durations. These measurements are also compared against the known glucose concentration in the medium that the reference BG meter strip takes its measurement from. Any possible bias and offset correction as a function of the difference between the primary and secondary reference BG meter algorithm outputs as well as the duration of the extended time, can then be used to correct the reference BG meter reading used for calibration in the analyte measurement system. This online correction will be applied as soon as the secondary reference BG meter algorithm finishes. The calibration algorithm in the analyte measurement system can then be used to revise the sensitivity value based on the bias and/or offset adjusted reference BG meter reading.

In some embodiments, the correlation between the degree of certainty of a reference BG meter reading and the difference between primary and secondary reference BG meter algorithm outputs as a function of extended time duration is obtained. In an online implementation, as soon as the secondary reference BG meter algorithm finishes, the weighting of the latest sensitivity value can be adjusted by taking into account for the degree of certainty obtained offline.

Figure 4:
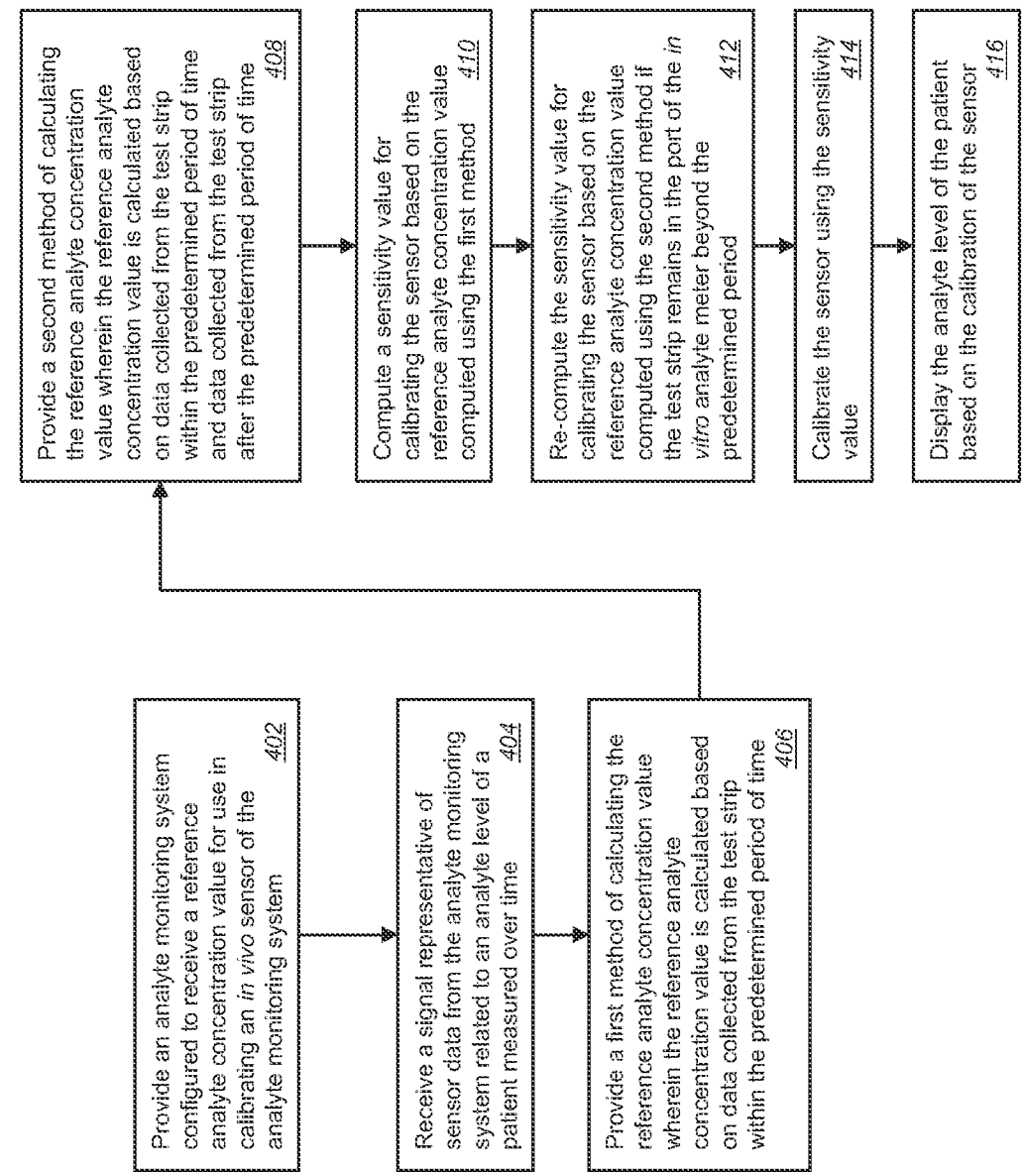
FIG. 4 depicts a flowchart illustrating an example of a fourth method for calibrating a sensor of an analyte monitoring system in accordance with some embodiments of the present disclosure.

Turning now to FIG. 4, an example embodiment of a method 400 is depicted as a flowchart. An analyte monitoring system is provided that is configured to receive a reference analyte concentration value for use in calibrating an in vivo sensor of the analyte monitoring system (402). The reference analyte concentration value is calculated based on a test strip inserted in a port of an in vitro analyte meter for a predetermined period of time. A signal representative of sensor data is received from the analyte monitoring system related to an analyte level of a patient measured over time (404). A first method of calculating the reference analyte concentration value is provided wherein the reference analyte concentration value is calculated based on data collected from the test strip within the predetermined period of time (406). A second method of calculating the reference analyte concentration value is provided wherein the reference analyte concentration value is calculated based on data collected from the test strip within the predetermined period of time and data collected from the test strip after the predetermined period of time (408). A sensitivity value is computed for calibrating the sensor based on the reference analyte concentration value computed using the first method (410). The sensitivity value for calibrating the sensor is re-computed based on the reference analyte concentration value computed using the second method if the test strip remains in the port of the in vitro analyte meter beyond the predetermined period (412). The sensor is calibrated using the sensitivity value (414). The analyte level of the patient is displayed based on the calibration of the sensor (416).

Figure 5:
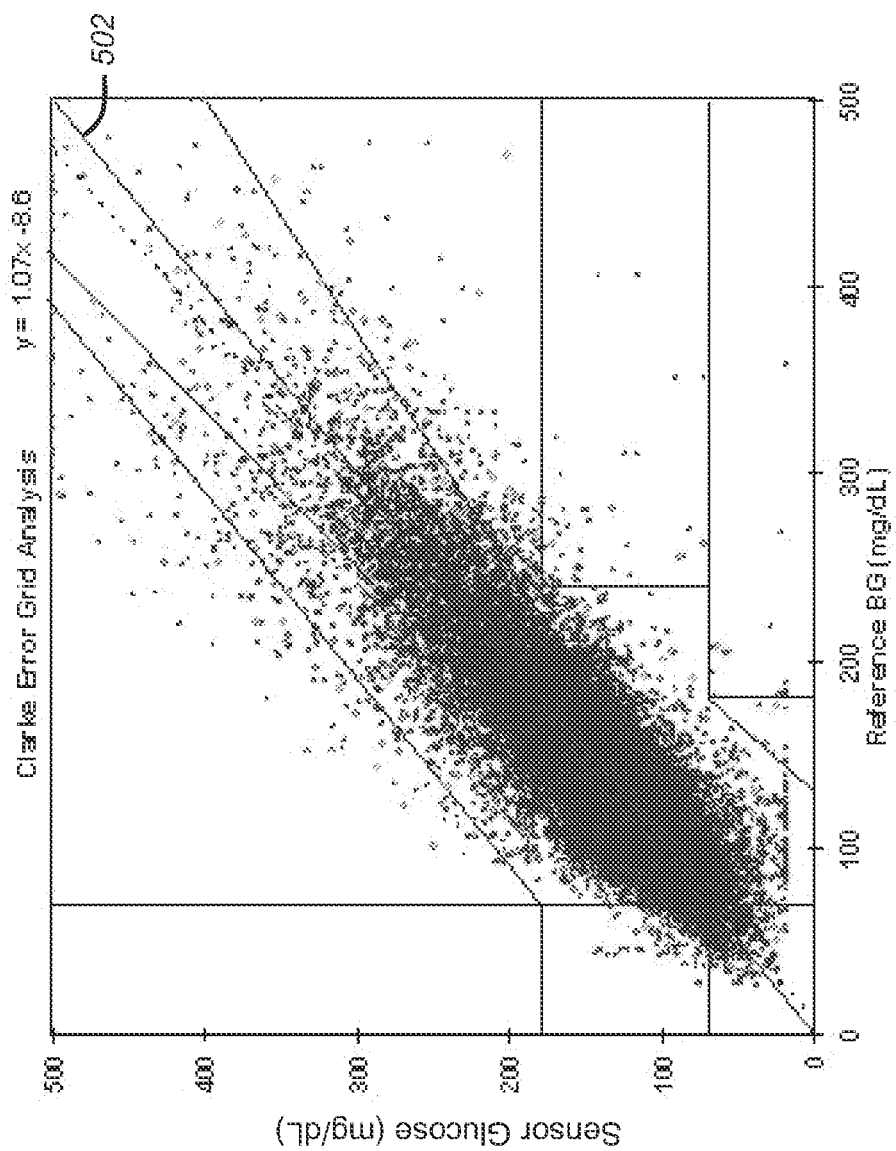
FIG. 5 depicts a graph of example data on a Clarke error grid in accordance with some embodiments of the present disclosure.
Figure 6:
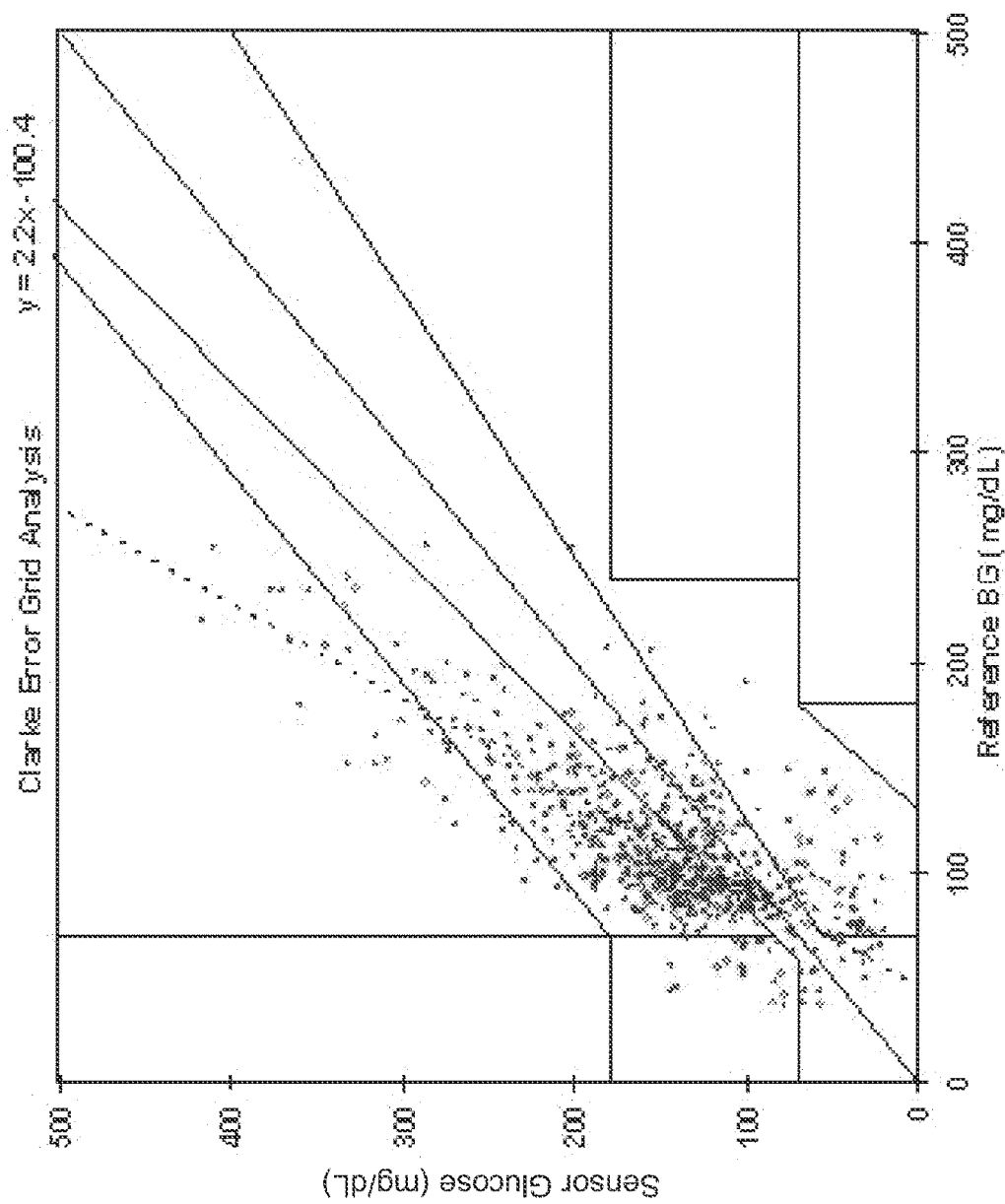
FIG. 6 depicts a graph of example data on a Clarke error grid in accordance with some embodiments of the present disclosure.

FIG. 5 depicts a Clarke Grid 500 of sensor data and reference BG points from a collection of experiments. The Clarke Grid shows a certain amount of data dispersion on the higher end. To relate to the ESA case, a subset of the data presented in FIG. 5 is shown in FIG. 6. In FIG. 6, only paired points where calibration took place during repressed sensitivity are displayed. As sensitivity recovers to its regular value, which is higher relative to when sensitivity is repressed, the sensor glucose values tend to display higher numbers. Composite sensitivity (Sc) is the effective sensitivity used to determine displayed glucose values at each data sample instance. As an illustrative example, the data points in Clarke Grid 600 in FIG. 6 are restricted to points whose calibration sensitivity value, Sc, is less than or equal to $7/10^{th}$ of the true sensitivity. True sensitivity is computed after the fact from the median of all available sensitivities, Sm. Note that this subset of the population is the group that contributes to the high-end scatter seen in FIG. 5. As the stratification is changed from $7/10^{th}$ to $8/10^{th}$, and so on, more and more of the high-end scatter seen in FIG. 5 will get included, and less and less of the ideal scatter near the 45 degree line 502 will get excluded.

Figure 7:
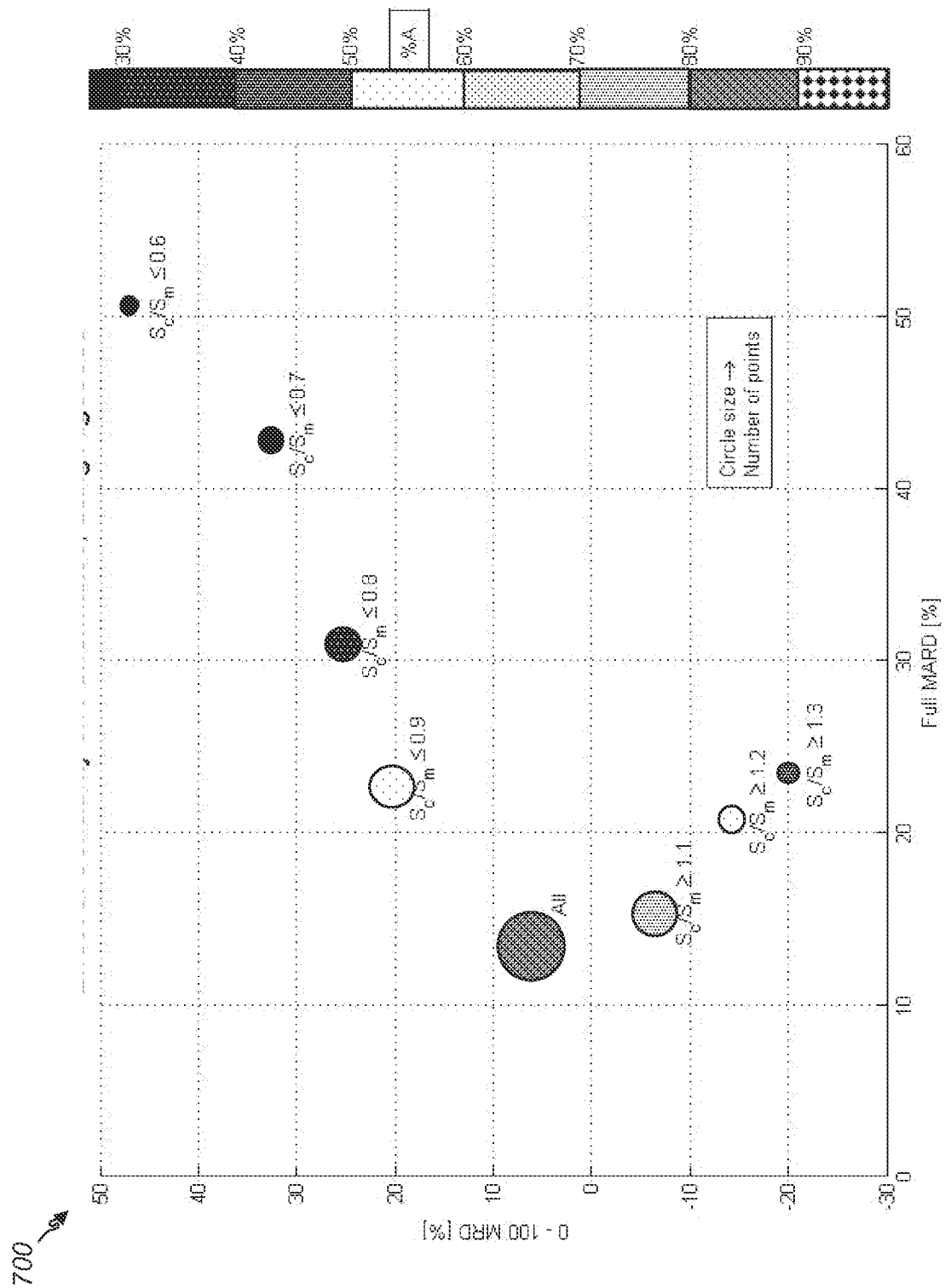
FIG. 7 depicts a graph summarizing the effect of stratifying the example data in FIG. 5 in accordance with some embodiments of the present disclosure.

FIG. 7 summarizes the effect of stratifying the data in FIG. 5 based on the ratio between the sensitivity during calibration, Sc, and the best estimate of true sensor sensitivity, Sm. The horizontal axis is the overall MARD (Mean Absolute Relative Difference) of each group, which is a metric that roughly describes the variability of the accuracy. The vertical axis is the low end MRD (Mean Relative Difference) of each group, which is a metric that roughly describes low-end bias of the accuracy. The relative size of each circle reflects the number of paired points that fall into each group, with the "All" group having the largest number of paired points. The patterns are indicative of the Percent A region of the Clarke Grid Statistics of each group, closer to the bottom being a higher Percent A value than closer to the top.

The stratification based on Sc/Sm ratio shown in FIG. 7 is presented in 10% increments from the full population (i.e. "All" group). The groups below median are those whose Sc/Sm values are less than or equal to 0.9, 0.8, 0.7 and 0.6. Similarly, the groups above median are those whose Sc/Sm values are greater than or equal to 1.1, 1.2, and 1.3. There are not enough points for the 1.4 group.

Given the equal 10% increments, it can be observed that the performance degradation in terms of marginal increase in full MARD, marginal increase in the absolute value of low end MRD, and the marginal decrease in Percent A, moves faster for the groups below the median than for the groups above the median. Practically, this means that based on the common accuracy performance metrics, the system is much more robust to a high sensitivity calibration compared to a low sensitivity calibration of the same additive percentage change. This is still the case if the comparison were to be made in the geometric percentage change sense. For example, the group where Sc/Sm is less than or equal to 0.8 should be geometrically comparable to the group where Sc/Sm is greater than or equal to 1/0.8=1.25. One would expect that this group would lie between the 1.2 and 1.3 groups in FIG. 5. While the low end MRD is not significantly different, the MARD and percent A statistics are worse for the 0.8 group.

In the general context of calibration, it can be assumed that the effective sensitivity being somewhat higher than computed is preferred over using the "as is" value or a mildly scaled down value. This observation can be combined with real-time observations of past calibrations as well as aggregate sensor sensitivity information obtained from the manufacturing lot to improve the robustness of each calibration instance. In the particular case related to ESA, where early sensitivity calculations are most likely to be underestimated, a proper scaling of this calculated value could mean improved accuracy.

Prior information regarding the sensor based on past calibrations and/or sample lot statistics is used to obtain the best nominal estimate of the sensor sensitivity. Any statistical property of this estimate, such as mean and standard deviation, can be adjusted by the risk distribution derived by information obtained from the process summarized in FIG. 10. The result is a table of correction factors on each calibration instance based on how the current calibration value compares to prior information. This table could also be a function of elapsed time since sensor start as well as elapsed time since the last calibration. For example, instead of using median sensitivity to normalize all Sc values after the fact, nominal sensor code sensitivity can be used to normalize the Sc values. A plot similar to plot 700 in FIG. 7 can then be obtained. Using this inference, a risk distribution can be obtained, where, for any given calibration, the computed sensitivity is compared to the nominal sensor code sensitivity, and a correction factor is applied to the computed sensitivity based on this comparison. In this example, the correction factor table can be obtained a priori from a database of sensor use. The correction factor table can be periodically reviewed offline to determine whether any adjustment is necessary to the algorithm. Another example would be to compute the median sensitivity based on all past calibration attempts plus the nominal sensor code sensitivity to revise the correction factor table previously described in real time during each sensor wear. The present disclosure uses information regarding the effect of over and under estimation of computed sensitivity with respect to common performance metrics such as, but not limited to low end MRD, full MRD, MARD, Clarke Grid Percent A, best fit line intercept, and root mean squared error (RMSE).

Figure 8:
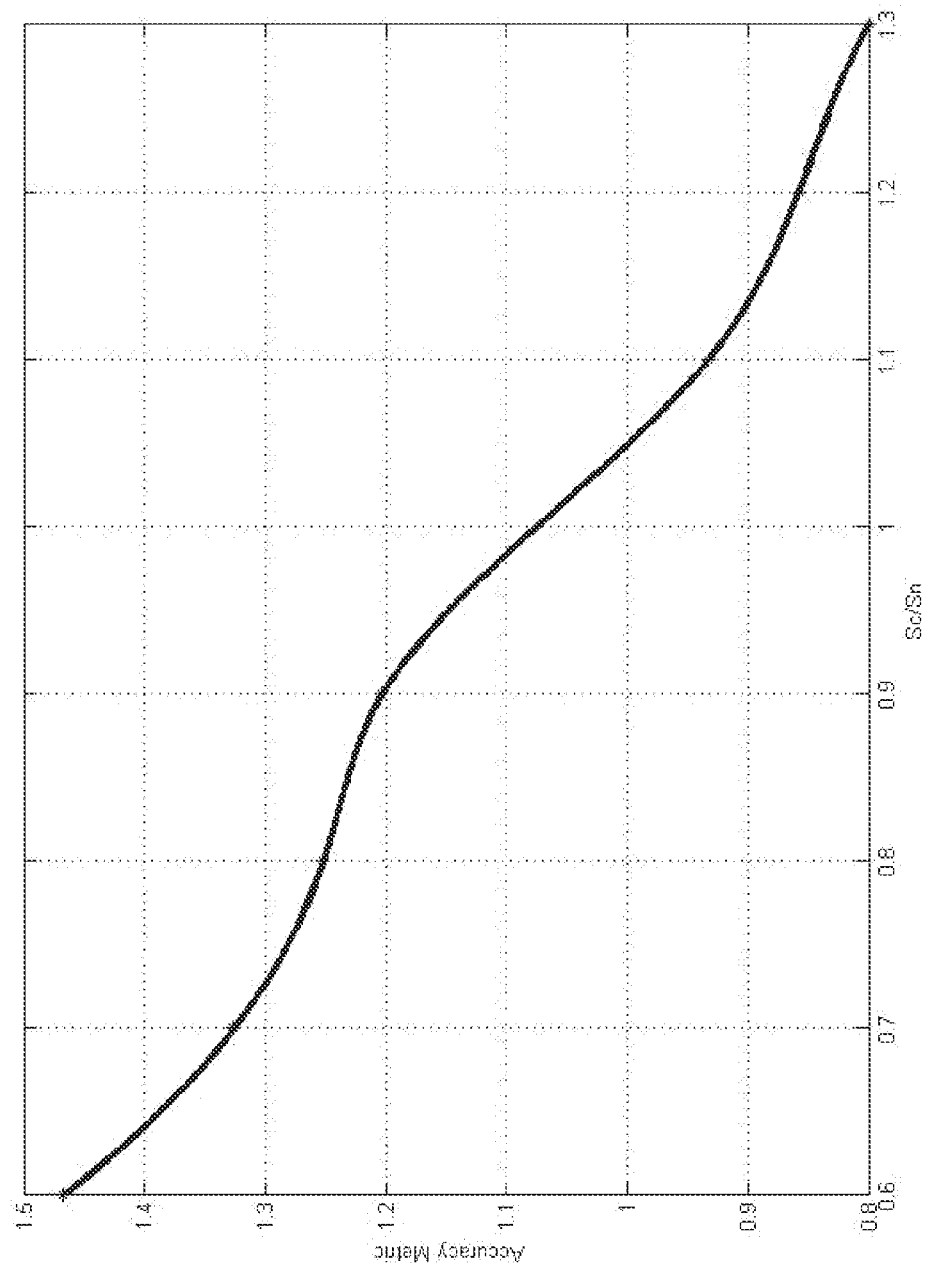
FIG. 8 depicts a graph of an example correlation between an accuracy metric and the ratio of calibration sensitivity (Sc) to ideal sensitivity (Sn) in accordance with some embodiments of the present disclosure.
Figure 9:
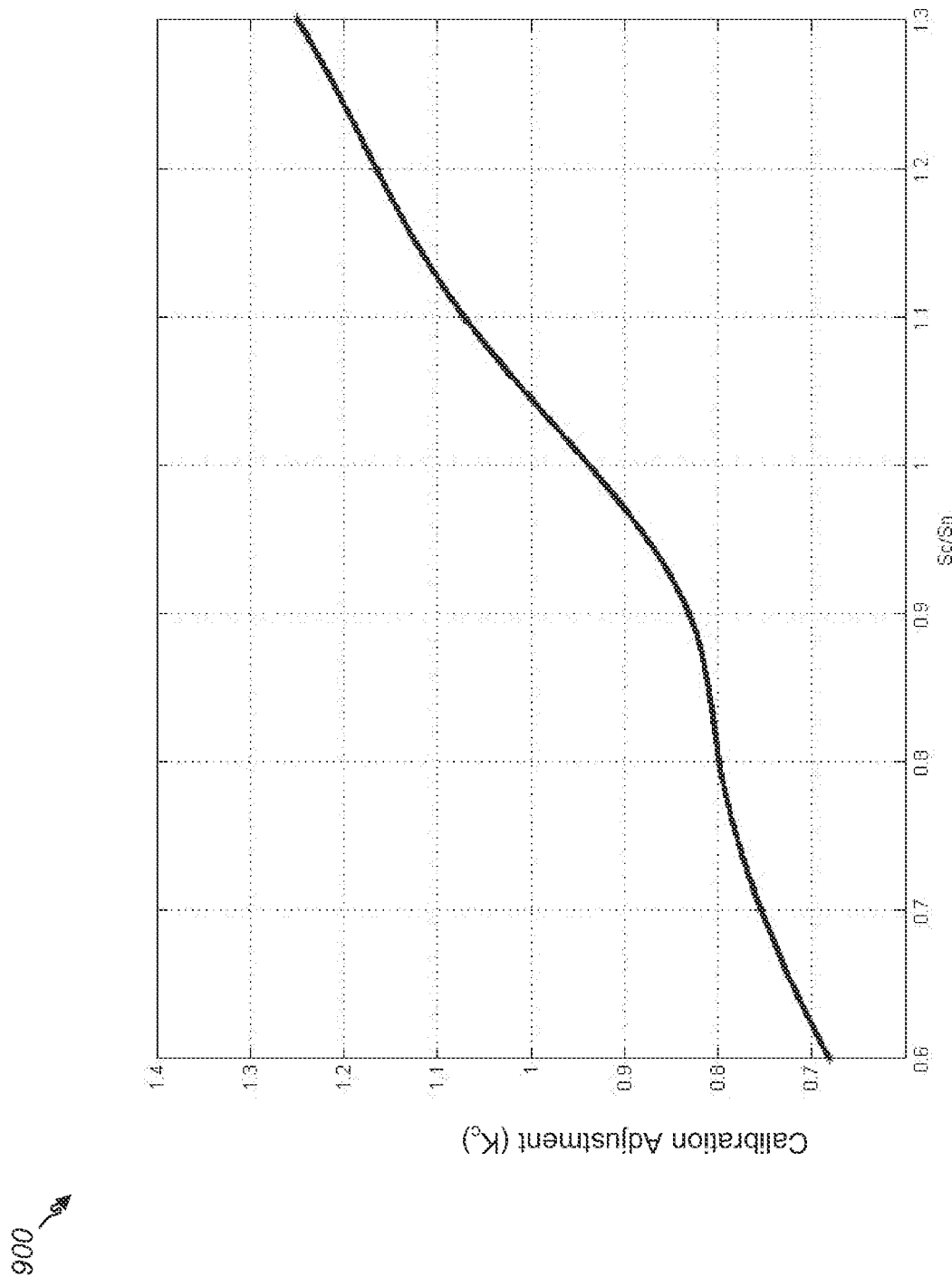
FIG. 9 depicts a graph of an example of a calibration adjustment factor derived by inverting the relative accuracy metric of FIG. 8 in accordance with some embodiments of the present disclosure.
Figure 10:
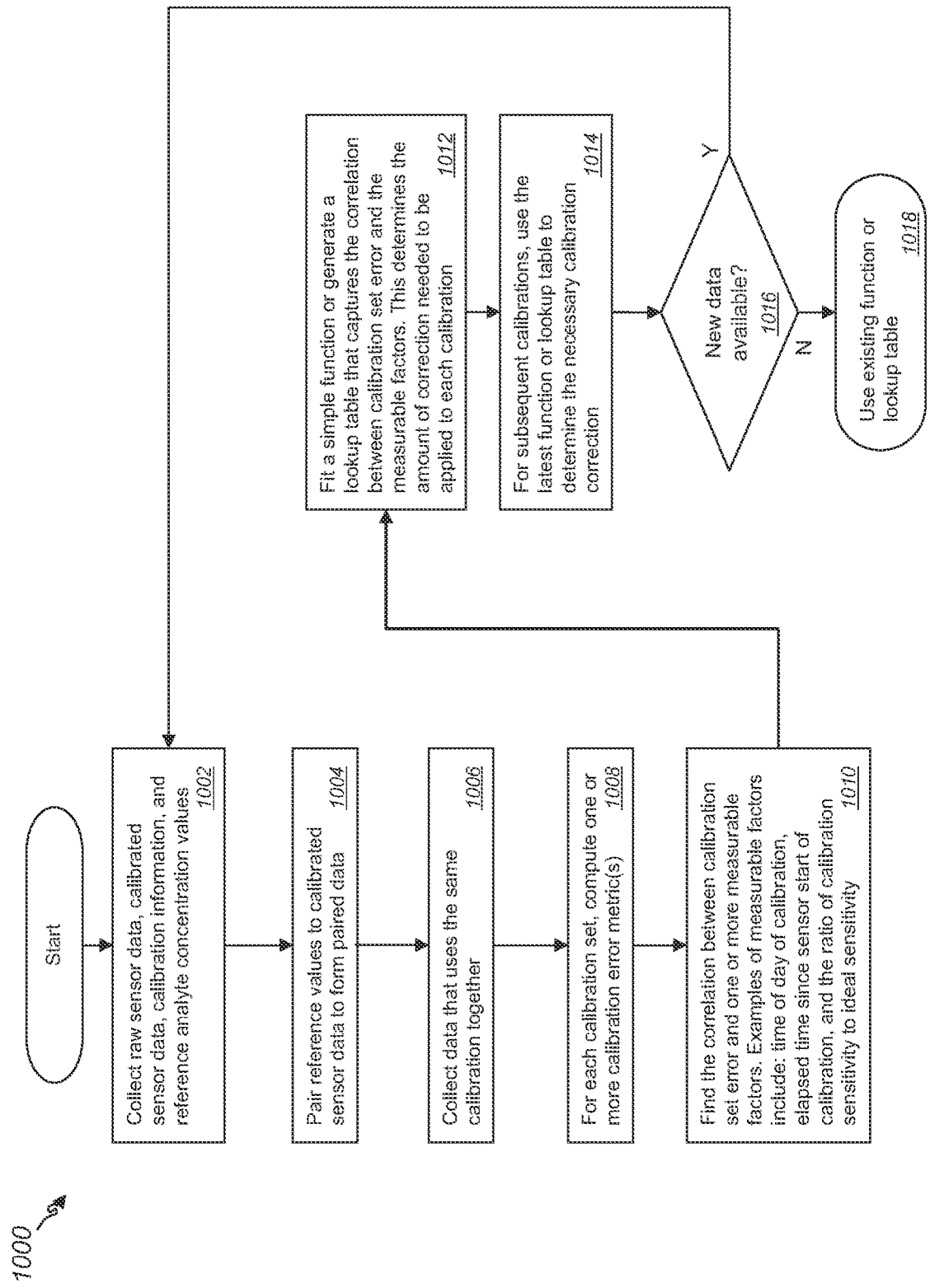
FIG. 10 depicts a flowchart illustrating an example of a fifth method for calibrating a sensor of an analyte monitoring system in accordance with some embodiments of the present disclosure.

FIG. 8 is a graph 800 depicting an example correlation between an accuracy metric and the ratio of calibration sensitivity (Sc) to ideal sensitivity (Sn). FIG. 9 is a graph 900 depicting an example of a calibration adjustment factor derived by inverting the relative accuracy metric of FIG. 8. Turning to FIG. 10, a flowchart detailing an example embodiment of a method 1000 for determining an adjustment to a calibration based on the correlation of calibration error, calibrated sensitivity, and ideal sensitivity according to the present disclosure, is shown. Paired reference BG data and calibrated sensor data are collected (1002). The data is paired (1004) and grouped based on the calibration used (1006). Each "calibration" set contains applicable paired data, the calibration sensitivity, and the ideal sensitivity. Calibration sensitivity may be either immediate or composite sensitivity. Ideal sensitivity may require raw sensor data and reference values from the past. One or more accuracy metrics are selected to be used as a basis of the adjustment (1008). For example, mean relative difference (MRD) of paired values below 100 mg/dL. A correlation is found between the accuracy metric and the ratio of calibration sensitivity (Sc) to ideal sensitivity (Sn) (1010). For example, the ideal sensitivity can be the sensor-code-based sensitivity as depicted in FIG. 8. Based on the correlation, the calibration adjustment is computed, either as a lookup table (for different ranges of Sc/Sn values) or a continuous function (1012). For example, given the relative accuracy metric above, the calibration adjustment becomes a relative value. So that adjusted glucose Ga is a function of raw glucose Gr, calibration sensitivity Sc, and the calibration adjustment Kc (labeled as Glucose Correction Factor in FIG. 9).

$$Ga = Kc \; Gr/Sc, \text{ where } Kc \text{ is the inverse of the Accuracy Metric.}$$

For an additive accuracy metric such as Mean Difference, the adjustment is:

$$Ga = (Gr/Sc) + Kc, \text{ where } Kc \text{ is the negative of the Accuracy Metric.}$$

For subsequent calibrations, the latest function or lookup table is used to determine the necessary calibration correction (1014). The method 1000 repeats if new data becomes available (1016) or otherwise uses the latest function or lookup table (1018).

Figure 11:
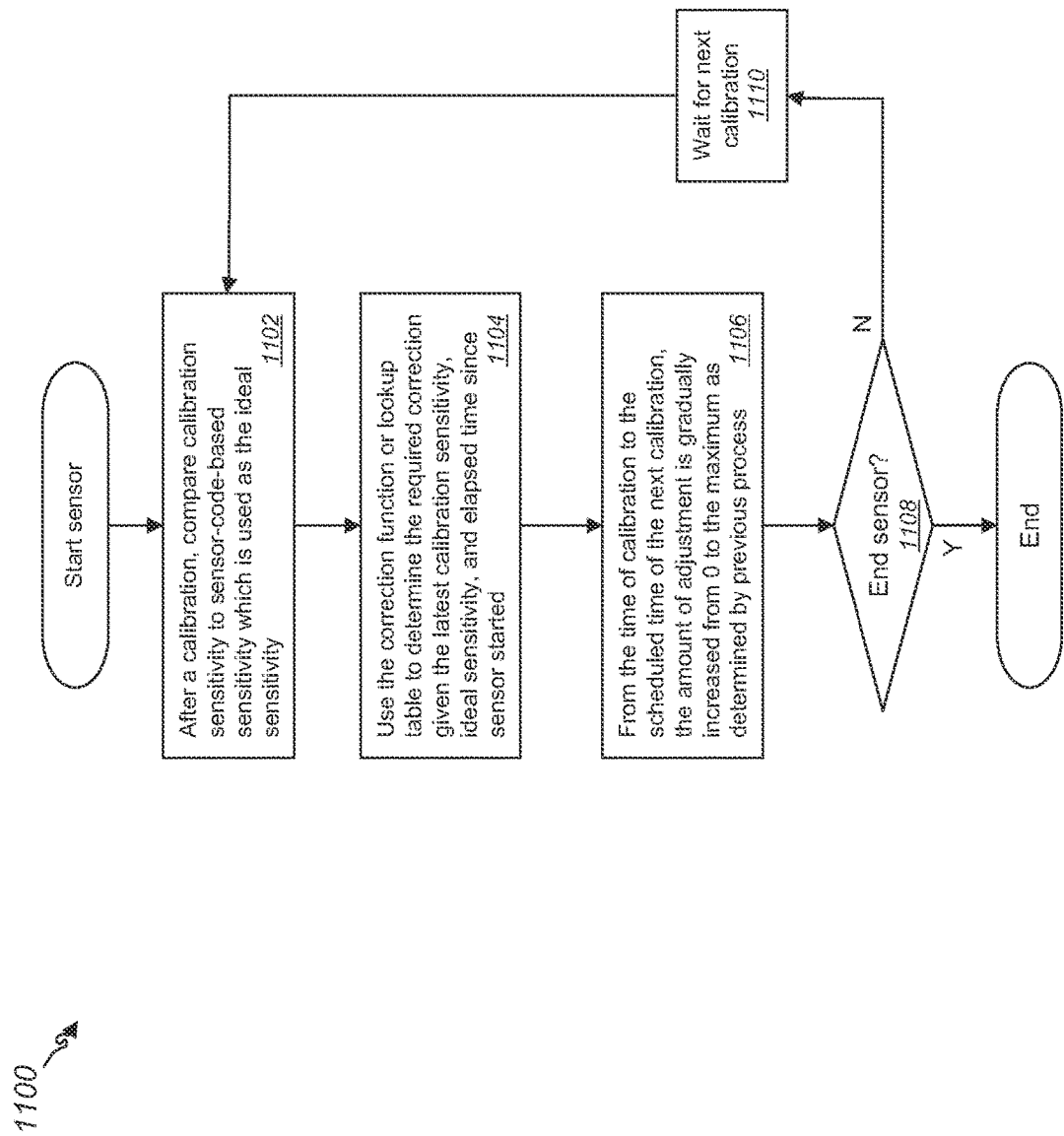
FIG. 11 depicts a flowchart illustrating an example of a sixth method for calibrating a sensor of an analyte monitoring system in accordance with some embodiments of the present disclosure.

FIG. 11 is a flowchart detailing an example embodiment of a method 1100 for applying an adjustment to a calibration in real-time according to the present disclosure. Once the in vivo sensor of an analyte monitoring system has been started and an initial calibration completed, the calibration sensitivity is compared to the sensor-code-based sensitivity (1102). The sensor-code-based sensitivity is used as the ideal sensitivity. The correction function or lookup table is next used to find out the required correction given the latest calibration sensitivity, ideal sensitivity, and elapsed time since sensor started (1104). From the time of calibration to the scheduled time to the next calibration, the amount of adjustment is gradually increased from 0 to the maximum as determined by the previous process (1106). The adjustment modifies how the calibration sensitivity transforms raw signal into glucose concentration units. If the sensor is still active (1108), the method 1100 waits for the next calibration (1110) and then repeats. Otherwise, the method 1100 ends.

Figure 12:
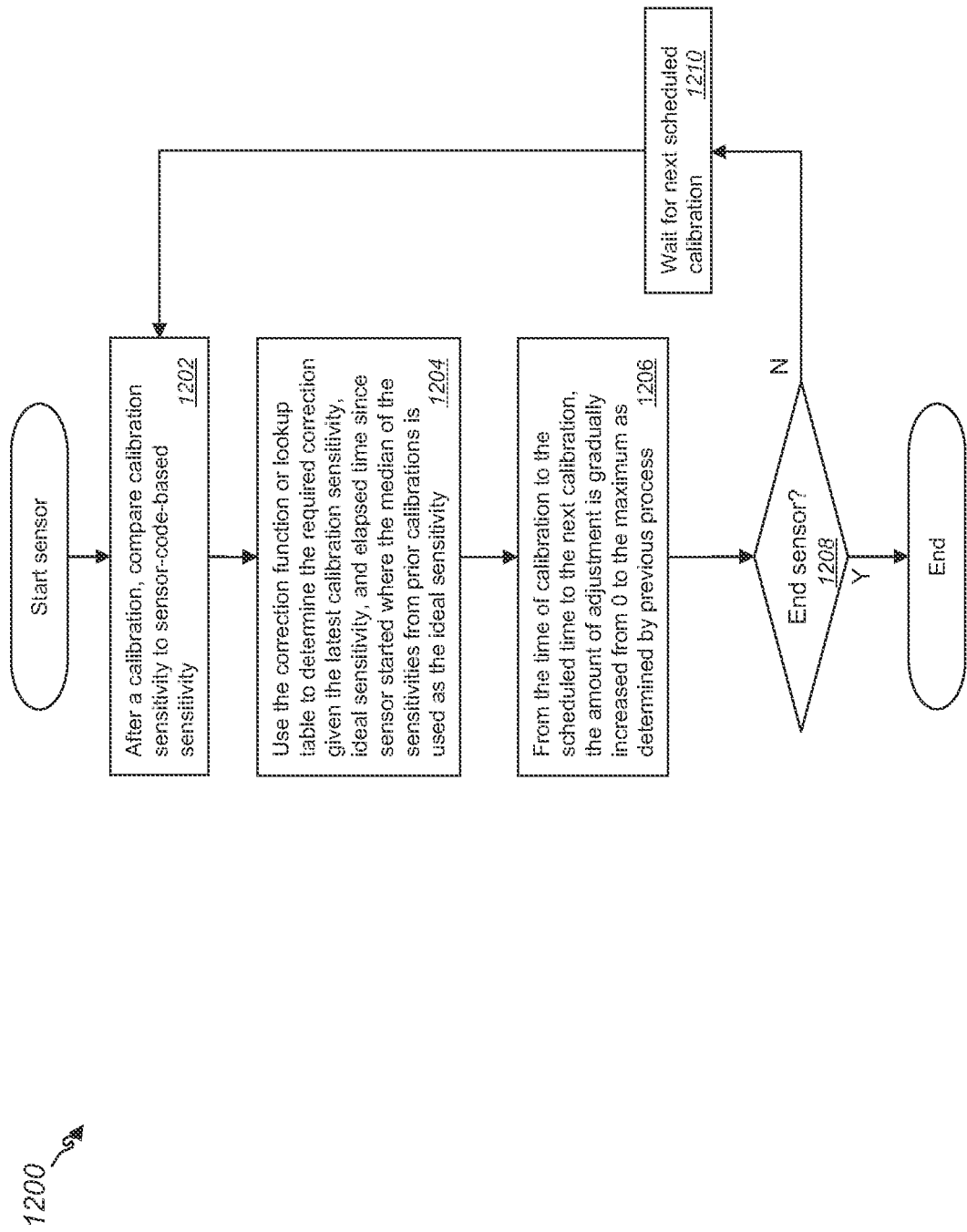
FIG. 12 depicts a flowchart illustrating an example of a seventh method for calibrating a sensor of an analyte monitoring system in accordance with some embodiments of the present disclosure.

FIG. 12 is a flowchart detailing an example embodiment of an alternative method 1200 for applying an adjustment to a calibration in real-time according to the present disclosure. Once the in vivo sensor of an analyte monitoring system has been started and an initial calibration completed, the calibration sensitivity is compared to the sensor-code-based sensitivity (1202). In this embodiment, the median of the sensitivities from prior calibrations is used as the ideal sensitivity. The correction function or lookup table is then used to determine the required correction given the latest calibration sensitivity, ideal sensitivity, and elapsed time since sensor started (1204). From the time of calibration to the scheduled time to the next calibration, the amount of adjustment is gradually increased from 0 to the maximum as determined by the previous process (1206). The adjustment modifies how the calibration sensitivity transforms raw signal into glucose concentration units. If the sensor is still active (1208), the method 1200 waits for the next calibration (1210) and then repeats. Otherwise, the method 1200 ends.

Accordingly, in certain embodiments, a computer-implemented method includes receiving a signal representative of sensor data from an analyte sensor configured to monitor an analyte level over time, calibrating the analyte sensor if attenuation of the received signal from the analyte sensor is not detectable, deferring calibration of the analyte sensor if attenuation of the received signal from the analyte sensor is detectable when calibration is requested, wherein the calibration is deferred until the attenuation of the received signal is no longer detected, storing the signal from the analyte sensor for a period of time spanning from before the calibration to after the calibration, determining whether a previously undetected signal attenuation has occurred during the calibration based on the stored signal after the calibration has been completed, performing reconstruction of the received signal based on the stored signal from the analyte sensor for the period of time spanning from before the calibration to after the calibration, when it is determined that the previously undetected signal attenuation has occurred, to generate a reconstructed signal, updating the calibration of the analyte sensor based on the reconstructed signal, and invalidating the calibration of the analyte sensor and requesting a new calibration of the analyte sensor if performing the reconstruction of the received signal does not generate the reconstructed signal.

Certain embodiments further include displaying an analyte concentration value corresponding to the monitored analyte level if the previously undetected signal attenuation did not occur during calibration based on the stored signal, or if performing the reconstruction of the received signal generated the reconstructed signal.

Certain embodiments also include suspending displaying the analyte concentration value if the calibration of the analyte sensor is invalidated and the previously undetected signal attenuation is greater than a predefined threshold.

Certain embodiments further include displaying an analyte concentration value when the new calibration is performed and the previously undetected signal attenuation is less than a predefined threshold.

Certain embodiments further include delaying invalidating the calibration if the signal attenuation is determined to be continuing to occur.

In certain embodiments, deferring calibration if attenuation of the signal from the analyte sensor is detectable further includes detecting signal attenuation from at least one of a hardware system condition, an environmental condition, and a physiological condition.

In certain embodiments, deferring calibration if attenuation of the signal from the analyte sensor is detectable further includes detecting signal attenuation from at least one of early signal attenuation and a dropout.

A system for monitoring an analyte using an in vivo sensor in accordance with an embodiment of the present disclosure includes a processor, a memory operatively coupled to the processor, the memory storing instructions which, when executed by the processor, causes the processor to: receive a signal representative of sensor data from an analyte sensor configured to monitor an analyte level over time, calibrate the analyte sensor if attenuation of the received signal from the analyte sensor is not detectable, defer calibration of the analyte sensor if attenuation of the received signal from the analyte sensor is detectable when calibration is requested, wherein the calibration is deferred until the attenuation of the received signal is no longer detected, store the signal from the analyte sensor for a period of time spanning from before the calibration to after the calibration, determine whether a previously undetected signal attenuation has occurred during the calibration based on the stored signal after the calibration has been completed, perform reconstruction of the received signal based on the stored signal from the analyte sensor for the period of time spanning from before the calibration to after the calibration, when it is determined that the previously undetected signal attenuation has occurred, to generate a reconstructed signal, update the calibration of the analyte sensor based on the reconstructed signal, and invalidate the calibration of the analyte sensor and request a new calibration of the analyte sensor if performing the reconstruction of the received signal does not generate the reconstructed signal.

A computer program product stored on a computer-readable medium in accordance with one embodiment of the present disclosure includes instructions to: receive a signal representative of sensor data from an analyte sensor configured to monitor an analyte level over time, calibrate the analyte sensor if attenuation of the received signal from the analyte sensor is not detectable, defer calibration of the analyte sensor if attenuation of the received signal from the analyte sensor is detectable when calibration is requested, wherein the calibration is deferred until the attenuation of the received signal is no longer detected, store the signal from the analyte sensor for a period of time spanning from before the calibration to after the calibration, determine whether a previously undetected signal attenuation has occurred during the calibration based on the stored signal after the calibration has been completed, perform reconstruction of the received signal based on the stored signal from the analyte sensor for the period of time spanning from before the calibration to after the calibration, when it is determined that the previously undetected signal attenuation has occurred, to generate a reconstructed signal, update the calibration of the analyte sensor based on the reconstructed signal, and invalidate the calibration of the analyte sensor and request a new calibration of the analyte sensor if performing the reconstruction of the received signal does not generate the reconstructed signal.

Certain embodiments include a computer-implemented method comprising defining a set of system checks associated with an analyte monitoring system, receiving a signal representative of sensor data from an analyte monitoring system related to an analyte level of a patient measured over time, receiving a reference analyte concentration value, calculating a sensitivity value based on the signal and the reference analyte concentration value, performing the system checks on the sensitivity value, determining if the signal is a cause of the sensitivity value being invalid if the system checks indicate the sensitivity value is invalid, determining if the reference analyte concentration value is a cause of the sensitivity value being invalid if the system checks indicate the sensitivity value is invalid, recalculating the sensitivity value using new sensor data after a delay if the signal was a cause of the sensitivity value being invalid, recalculating the sensitivity value using a new reference analyte concentration value if the reference analyte concentration value was a cause of the sensitivity value being invalid, and displaying the analyte level of the patient based on the recalculated sensitivity value if the system checks indicate the sensitivity value is invalid.

In certain embodiments, determining if the reference analyte concentration value is a cause of the sensitivity value being invalid includes determining if a difference between the reference analyte concentration value and a prior reference analyte concentration value is larger than a predefined threshold amount wherein the prior reference analyte concentration value was received within a predefined time period of the reference analyte concentration value.

In certain embodiments, determining if the reference analyte concentration value is a cause of the sensitivity value being invalid includes determining if a difference between a standard deviation of the reference analyte concentration value and a standard deviation of a predicted reference analyte concentration is larger than a predefined threshold amount, wherein the standard deviation of the predicted reference analyte concentration is determined based on a plurality of prior reference analyte concentration values.

In certain embodiments, determining if the signal is a cause of the sensitivity value being invalid includes determining if a difference between the signal and a prior signal received during a prior calculation of a sensitivity value is larger than a predefined threshold amount wherein the prior signal was received within a predefined time period of the signal.

In certain embodiments, determining if the signal is a cause of the sensitivity value being invalid includes determining if the signal correlates with prior signals received during prior calculations of sensitivity values to within a predetermined amount.

In certain embodiments, determining if the signal is a cause of the sensitivity value being invalid includes determining if including the signal in a moving average population of prior signals received during prior calculations of sensitivity values changes a rate of change distribution of the moving average population by more than a predetermined threshold.

Certain embodiments may further comprise calculating a weighting of the sensitivity value indicative of a relative confidence rating of the accuracy of the sensitivity value, wherein the weighting is determined based on the signal and the reference analyte concentration value compared to prior signals and the reference analyte concentration values received during prior calculations of sensitivity values.

Certain embodiments include a computer-implemented method comprising providing an analyte monitoring system configured to request a reference analyte concentration value for use in calibrating an in vivo sensor of the analyte monitoring system, wherein the request may be satisfied by a user initiated supply of the reference analyte concentration value before the request or by a user response to the request, receiving a signal representative of sensor data from the analyte monitoring system related to an analyte level of a patient measured over time, providing a first method of computing a sensitivity value for calibrating the sensor wherein the sensitivity value is computed based on an amount of sensor data that is less than a predetermined amount, providing a second method of computing a sensitivity value for calibrating the sensor wherein the sensitivity value is computed based on an amount of sensor data that is more than a predetermined amount, calibrating the sensor using the first method when the request is satisfied by a user response to the request, calibrating the sensor using the second method when the request is satisfied by a user initiated supply of the reference analyte concentration before the request, and displaying the analyte level of the patient based on the calibration of the sensor.

In certain embodiments, if the user initiated supply of the reference analyte concentration occurs within a predetermined time before the request, the sensor is calibrated using the first method.

In certain embodiments, if the user supplies a reference analyte concentration before the request and a second reference analyte concentration in response to the request, a sensitivity value is computed for each analyte concentration and a weighted average of the sensitivity values is used for calibration.

In certain embodiments, if the user supplies two or more reference analyte concentrations before the request, a sensitivity value is computed for each analyte concentration and a weighted average of the sensitivity values is used for calibration.

In certain embodiments, if the user initiated supply of the reference analyte concentration occurs within a predetermined time before the request and a sensitivity value based on the second method passes an acceptance criteria, the system cancels the request and the sensor is calibrated using the second method.

Certain embodiments may further comprise defining a set of acceptance criteria for using a sensitivity value to calibrate the sensor, wherein if the user supplies two or more reference analyte concentrations, a sensitivity value is computed for each analyte concentration and the sensor is calibrated based on only sensitivity values that pass the acceptance criteria.

Certain embodiments include a computer-implemented method comprising providing an analyte monitoring system configured to receive a reference analyte concentration value for use in calibrating an in vivo sensor of the analyte monitoring system, wherein the reference analyte concentration value is calculated based on a test strip inserted in a port of an in vitro analyte meter for a predetermined period of time, receiving a signal representative of sensor data from the analyte monitoring system related to an analyte level of a patient measured over time, providing a first method of calculating the reference analyte concentration value wherein the reference analyte concentration value is calculated based on data collected from the test strip within the predetermined period of time, providing a second method of calculating the reference analyte concentration value wherein the reference analyte concentration value is calculated based on data collected from the test strip within the predetermined period of time and data collected from the test strip after the predetermined period of time, computing a sensitivity value for calibrating the sensor based on the reference analyte concentration value computed using the first method, re-computing the sensitivity value for calibrating the sensor based on the reference analyte concentration value computed using the second method if the test strip remains in the port of the in vitro analyte meter beyond the predetermined period, calibrating the sensor using the sensitivity value, and displaying the analyte level of the patient based on the calibration of the sensor.

Certain embodiments may further comprise determining a first value indicative of a variability of the reference analyte concentration value; determining a second value indicative of a variability of the sensitivity value based on the first value; and verifying validity of a subsequent calibration attempt using a subsequently computed sensitivity value based on the second value.

Certain embodiments may further comprise recursively re-computing the reference analyte concentration value based on data collected from the test strip within the predetermined period of time and data collected from the test strip after each additional passage of the predetermined period of time or fraction thereof.

In certain embodiments, re-computing the sensitivity value includes using a weighted average of the reference analyte concentration values computed using the first method and the second method.

In certain embodiments, the weighting is determined based upon historical differences between reference analyte concentration values computed using the first method and the second method.

In certain embodiments, the historical differences between reference analyte concentration values computed using the first method and the second method include reference analyte concentration values computed using the second method wherein the test strip remains in the port of the in vitro analyte meter for varying amounts of time.

Certain embodiments include a computer-implemented method comprising providing an analyte monitoring system configured to receive a reference analyte concentration value for use in calibrating an in vivo sensor of the analyte monitoring system, wherein the reference analyte concentration value is calculated based on a test strip inserted in a port of an in vitro analyte meter for a first predetermined period of time, receiving a signal representative of sensor data from the analyte monitoring system related to an analyte level of a patient measured over time, pairing the reference analyte concentration value with the sensor data in real time during the first predetermined period of time, calculating a first sensitivity value based on the reference analyte concentration value from the in vitro analyte meter during the first predetermined period of time, recursively updating the first sensitivity value for as long as the test strip remains in the port and can provide updated reference analyte concentration values, calculating a final sensitivity value after a second predetermined period of time based on sensor data up to the second predetermined time, paired with an updated reference analyte concentration value from a most recent recursive update.

In certain embodiments, the first predetermined period of time is approximately 3 seconds to approximately 10 seconds and wherein the second predetermined period of time is approximately 3 minutes to approximately 15 minutes.

Certain embodiments include a computer-implemented method comprising providing an analyte monitoring system configured to receive a reference analyte concentration value for use in calibrating an in vivo sensor of the analyte monitoring system, providing a nominal estimate of a sensitivity of the sensor based on at least one of past calibrations and sample lot statistics, adjusting one or more statistical properties of the nominal estimate based on a risk distribution, receiving a signal representative of sensor data from the analyte monitoring system related to an analyte level of a patient measured over time, computing a current sensitivity based on the reference analyte concentration value and the sensor data, determining a table of correction factors for each past calibration based on a comparison of a current sensitivity with prior sensitivity values, applying a correction factor from the table of correction factors to the computed current sensitivity to determine a corrected sensitivity, and displaying an analyte level of a patient based on the sensor being calibrated using the corrected sensitivity.

In certain embodiments, the risk distribution is derived by stratifying paired sensor data and reference analyte concentration values plotted on a Clarke Grid based on a ratio of sensor sensitivity during calibration and an estimate of true sensor sensitivity.

Certain embodiments include a computer-implemented method comprising providing an analyte monitoring system configured to receive a reference analyte concentration value for use in calibrating an in vivo sensor of the analyte monitoring system, receiving a signal representative of sensor data from the analyte monitoring system related to an analyte level of a patient measured over time, storing sensor data, calibrated sensor data, calibration information and reference analyte concentration values, pairing reference analyte concentration values with calibrated sensor data to form paired data, grouping paired data into calibration sets based on calibration sensitivity used for each paired data, computing one or more calibration error metrics for each calibration set, determining a correlation between the one or more calibration error metrics of the calibration sets and one or more measureable factors, determining a correction function that maps the determined correlation between the one or more calibration error metrics of the calibration sets and one or more measureable factors, computing a current sensitivity based on the reference analyte concentration value and the sensor data, applying a correction factor based on the correction function to the computed current sensitivity to determine a corrected sensitivity, and displaying an analyte level of a patient based on the sensor being calibrated using the corrected sensitivity.

In certain embodiments, the correction function is implemented as a look-up table.

In certain embodiments, the measureable factors include at least one of time of day of calibration, elapsed time since sensor start of calibration, and the ratio of calibration sensitivity to ideal sensitivity.

Certain embodiments may further comprise updating the correction function based on at least one of subsequently received sensor data, calibrated sensor data, calibration information and reference analyte concentration values.

Various other modifications and alterations in the structure and method of operation of the embodiments of the present disclosure will be apparent to those skilled in the art without departing from the scope and spirit of the present disclosure. Although the present disclosure has been described in connection with certain embodiments, it should be understood that the present disclosure as claimed should not be unduly limited to such embodiments. It is intended that the following claims define the scope of the present disclosure and that structures and methods within the scope of these claims and their equivalents be covered thereby.

What is claimed is:

1. A method for calibrating a signal generated by a glucose sensor indicative of a glucose level, comprising:
   storing, by at least one processor, a first sensitivity for the glucose sensor having an in vivo portion configured to be positioned in contact with an interstitial fluid of a user and an ex vivo portion;
   receiving, by the at least one processor, a prior calibrated glucose level data from a sensor electronics of the glucose sensor, wherein the calibrated glucose level data is based upon a signal generated by the glucose sensor over a first time period and indicative of the glucose level of the user;
   receiving, by the at least one processor, a reference blood glucose measurement of the user;
   pairing, by the at least one processor, the reference blood glucose measurement with the calibrated glucose level data to form a paired data;
   determining, by the at least one processor, an adjustment for the first sensitivity of the glucose sensor, wherein the adjustment includes a scaling factor determined based on the paired data, a distribution of sensor sensitivity, and a sensor start time;
   calibrating, by the at least one processor, the signal generated by the glucose sensor over a second time period after the first time period to corresponding glucose level data using the stored first sensitivity and the adjustment after the glucose sensor is positioned in contact with the interstitial fluid of the user; and
   transmitting, by the at least one processor, the glucose level data to a display unit.

2. The method of claim 1, wherein the first sensitivity includes a median sensitivity.

3. The method of claim 1, wherein the first sensitivity includes a mean sensitivity.

4. The method of claim 1, wherein the calibrating includes determining a second sensitivity for the glucose sensor using the adjustment and the first sensitivity.

5. The method of claim 1, further comprising storing the adjustment in a non-transitory memory of a sensor electronics for the glucose sensor.

6. The method of claim 5, wherein storing the adjustment comprises storing one or more correction factors in a table.

7. The method of claim 1, further comprising updating the adjustment in a non-transitory memory of the sensor electronics.

8. The method of claim 1, further comprising updating the adjustment in a non-transitory memory of the sensor electronics in real time.

9. The method of claim 1, wherein the first sensitivity includes a lot sensitivity of a plurality of glucose sensor of a manufacturing lot, and the plurality of glucose sensors includes the glucose sensor.

10. The method of claim 9, wherein the adjustment is based on a plurality of prior sensor uses of a subset of the plurality of glucose sensors of the manufacturing lot.

11. The method of claim 9, wherein the lot sensitivity includes a standard deviation.

12. The method of claim 1, further comprising:
    receiving, by the at least one processor, a second calibrated glucose level data from a sensor electronics of the glucose sensor, wherein the second calibrated glucose level data is based upon a second signal generated by the glucose sensor over a second time period and indicative of a second glucose level of the user;
    receiving, by the at least one processor, a second reference blood glucose measurement of the user;
    pairing, by the at least one processor, the second reference blood glucose measurement with the second calibrated glucose level data to form a second paired data; and
    determining, by the at least one processor, a second adjustment for the first sensitivity of the glucose sensor, wherein the second adjustment includes a second scaling factor determined based on the second paired data, the distribution of sensor sensitivity, and the sensor start time.

13. The method of claim 1, wherein the adjustment is determined based further on a correlation between a ratio of calibration sensitivity to ideal sensitivity and an accuracy metric.

14. The method of claim 1, wherein the reference blood glucose measurement comprises a user-initiated reference blood glucose measurement.

15. The method of claim 1, wherein the distribution of sensor sensitivity is a risk distribution.

16. The method of claim 1, wherein the adjustment comprises a function.

17. A device for calibrating a signal generated by a glucose sensor indicative of a glucose level, comprising:
    the glucose sensor having an in vivo portion configured to be positioned in contact with an interstitial fluid of a user;
    a non-transitory memory; and
    at least one processor communicatively coupled to the non-transitory memory and the glucose sensor and configured to:
       store a first sensitivity for the glucose sensor;
       receive a prior calibrated glucose level data from a sensor electronics of the glucose sensor, wherein the calibrated glucose level data is based upon a signal generated by the glucose sensor over a first time period and indicative of the glucose level of the user;
       receive a reference blood glucose measurement of the user;

pair the reference blood glucose measurement with the calibrated glucose level data to form a paired data;

determine an adjustment for the first sensitivity of the glucose sensor, wherein the adjustment includes a scaling factor determined based on the paired data, a distribution of sensor sensitivity, and a sensor start time;

calibrate the signal generated by the glucose sensor over a second time period after the first time period to corresponding glucose level data using the received first sensitivity and the determined adjustment after the glucose sensor is positioned in contact with the interstitial fluid of the user; and transmit the glucose level data to a display unit.

18. The device of claim 17, wherein the first sensitivity includes a median sensitivity.

19. The device of claim 17, wherein the first sensitivity includes a mean sensitivity.

20. The device of claim 17, wherein the at least one processor is configured to calibrate by determining a second sensitivity for the glucose sensor using the adjustment and the first sensitivity.

21. The device of claim 17, wherein the at least one processor is further configured to store the adjustment in the non-transitory memory.

22. The device of claim 21, wherein the at least one processor is configured to store the adjustment by at least storing one or more correction factors in a table.

23. The device of claim 17, wherein the at least one processor is further configured to update the adjustment in the non-transitory memory of the sensor electronics.

24. The device of claim 17, wherein the at least one processor is further configured to update the adjustment in the non-transitory memory of the sensor electronics in real time.

25. The device of claim 17, wherein the first sensitivity includes a lot sensitivity of a plurality of glucose sensor of a manufacturing lot, and the plurality of glucose sensors includes the glucose sensor.

26. The device of claim 25, wherein the adjustment is based on a plurality of prior sensor uses of a subset of the plurality of glucose sensors of the manufacturing lot.

27. The device of claim 25, wherein the lot sensitivity includes a standard deviation.

28. The device of claim 17, wherein the at least one processor is further configured to:

receive a second calibrated glucose level data from a sensor electronics of the glucose sensor, wherein the second calibrated glucose level data is based upon a second signal generated by the glucose sensor over a second time period and indicative of a second glucose level of the user;

receive a second reference blood glucose measurement of the user;

pair the second reference blood glucose measurement with the second calibrated glucose level data to form a second paired data; and determine a second adjustment for the first sensitivity of the glucose sensor, wherein the second adjustment includes a second scaling factor determined based on the second paired data, the distribution of sensor sensitivity, and the sensor start time.

29. The device of claim 17, wherein the adjustment is determined based further on a correlation between a ratio of calibration sensitivity to ideal sensitivity and an accuracy metric.

30. The device of claim 17, wherein the reference blood glucose measurement comprises a user-initiated reference blood glucose measurement.

31. The device of claim 17, wherein the distribution of sensor sensitivity is a risk distribution.

32. The device of claim 17, wherein the adjustment comprises a function.

* * * * *